US007824698B2

(12) United States Patent
Potts et al.

(10) Patent No.: US 7,824,698 B2
(45) Date of Patent: Nov. 2, 2010

(54) LYOPHILIZED FORMULATIONS OF SALINOSPORAMIDE A

(75) Inventors: Barbara Potts, Escondido, CA (US); Ramsharan Singh, San Diego, CA (US); Jan-Jon Chu, Carlsbad, CA (US); Bao Viet Mai, San Diego, CA (US); Natasha Reddinger, San Diego, CA (US); Cheryl (Billstrom) Sifferlen, San Diego, CA (US)

(73) Assignee: Nereus Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 12/025,679

(22) Filed: Feb. 4, 2008

(65) Prior Publication Data

US 2008/0188544 A1 Aug. 7, 2008

Related U.S. Application Data

(60) Provisional application No. 60/888,025, filed on Feb. 2, 2007, provisional application No. 60/986,891, filed on Nov. 9, 2007.

(51) Int. Cl.

| | |
|---|---|
| *A61K 9/00* | (2006.01) |
| *A61K 31/4965* | (2006.01) |
| *A61K 31/497* | (2006.01) |
| *A01N 43/38* | (2006.01) |
| *C07D 487/02* | (2006.01) |

(52) U.S. Cl. .................. 424/400; 514/421; 514/255.06; 514/254.11; 548/453

(58) Field of Classification Search ....................... None
See application file for complete search history.

(56) References Cited

U.S. PATENT DOCUMENTS

| | | | | |
|---|---|---|---|---|
| 5,008,294 | A * | 4/1991 | Neiss et al. | 514/731 |
| 5,445,829 | A | 8/1995 | Paradissis et al. | |
| 5,576,012 | A | 11/1996 | Bauer et al. | |
| 5,601,845 | A | 2/1997 | Buxton et al. | |
| 5,641,515 | A | 6/1997 | Ramtoola | |
| 5,653,987 | A | 8/1997 | Modi et al. | |
| 5,654,286 | A | 8/1997 | Hostetler | |
| 5,667,809 | A | 9/1997 | Trevino et al. | |
| 5,683,676 | A | 11/1997 | Akehurst et al. | |
| 5,688,529 | A | 11/1997 | Lidgate et al. | |
| 5,707,615 | A | 1/1998 | Cardin et al. | |
| 5,707,641 | A | 1/1998 | Gertner et al. | |
| 5,726,181 | A | 3/1998 | Hausheer et al. | |
| 5,733,888 | A | 3/1998 | Carver et al. | |
| 5,756,764 | A | 5/1998 | Fenteany et al. | |
| 5,874,443 | A | 2/1999 | Kiely et al. | |
| 5,886,210 | A | 3/1999 | Rayle et al. | |
| 5,922,683 | A | 7/1999 | Or et al. | |
| 6,133,308 | A | 10/2000 | Soucy et al. | |
| 6,147,223 | A | 11/2000 | Fenteany et al. | |
| 6,214,862 | B1 | 4/2001 | Fenteany et al. | |
| 6,271,199 | B2 | 8/2001 | Brand et al. | |
| 6,294,560 | B1 | 9/2001 | Soucy et al. | |
| 6,333,358 | B1 | 12/2001 | Nakazato et al. | |
| 6,335,358 | B1 | 1/2002 | Fenteany et al. | |
| 6,350,759 | B1 | 2/2002 | Casara et al. | |
| 6,458,825 | B1 | 10/2002 | Fenteany et al. | |
| 6,500,825 | B2 | 12/2002 | Lan et al. | |
| 6,506,787 | B2 | 1/2003 | Fujishita et al. | |
| 6,509,331 | B1 | 1/2003 | Audia et al. | |
| 6,566,553 | B2 | 5/2003 | Soucy et al. | |
| 6,645,999 | B1 | 11/2003 | Schreiber et al. | |
| 6,794,516 | B2 | 9/2004 | Soucy et al. | |
| 6,838,477 | B2 | 1/2005 | Schreiber et al. | |
| 6,849,743 | B2 | 2/2005 | Soucy et al. | |
| 7,144,723 | B2 | 12/2006 | Fenical et al. | |
| 7,176,232 | B2 | 2/2007 | Fenical et al. | |
| 7,176,233 | B2 | 2/2007 | Fenical et al. | |
| 7,179,834 | B2 | 2/2007 | Fenical et al. | |
| 7,183,417 | B2 | 2/2007 | Corey | |
| 7,276,530 | B2 | 10/2007 | Potts et al. | |
| 7,276,630 | B2 | 10/2007 | Dockner et al. | |
| 2001/0051654 | A1 | 12/2001 | Elliott et al. | |
| 2003/0157695 | A1 | 8/2003 | Fenical et al. | |
| 2004/0132692 | A1 * | 7/2004 | Sherrill et al. | 514/58 |
| 2004/0138196 | A1 | 7/2004 | Fenical et al. | |
| 2005/0049294 | A1 * | 3/2005 | Palladino et al. | 514/412 |
| 2005/0203029 | A1 | 9/2005 | Schubert et al. | |
| 2005/0203162 | A1 | 9/2005 | Xiao et al. | |
| 2006/0008852 | A1 | 1/2006 | Fenical et al. | |
| 2006/0229353 | A1 | 10/2006 | Stadler et al. | |
| 2006/0264495 | A1 | 11/2006 | Palladino et al. | |
| 2006/0287520 | A1 * | 12/2006 | Danishefsky et al. | 540/203 |
| 2007/0004676 | A1 | 1/2007 | Palladino et al. | |
| 2007/0155815 | A1 | 7/2007 | Fenical et al. | |
| 2007/0161693 | A1 | 7/2007 | Corey | |
| 2007/0225350 | A1 | 9/2007 | Anderson et al. | |
| 2008/0070273 | A1 | 3/2008 | Fenical et al. | |
| 2008/0070969 | A1 | 3/2008 | Potts et al. | |
| 2009/0069401 | A1 | 3/2009 | Fenical | |

FOREIGN PATENT DOCUMENTS

| | | |
|---|---|---|
| CA | 2429163 | 6/2002 |

(Continued)

OTHER PUBLICATIONS

BASF, Technical Information, 2004.*

(Continued)

*Primary Examiner*—Sreeni Padmanabhan
*Assistant Examiner*—Anna Pagonakis
(74) *Attorney, Agent, or Firm*—Knobbe Martens Olson & Bear LLP

(57) ABSTRACT

Lyophilized formulations comprising Salinosporamide A or analogs thereof are provided. In some aspects, lyophilized formulations comprising Salinosporamide A or analogs thereof and bulking agents are provided. Also provided are methods of lyophilizing Salinosporamide A or analogs thereof. In some aspects, a solvent or co-solvent system is utilized. Also provided are methods of administering Salinosporamide A or analogs thereof to patients.

14 Claims, 20 Drawing Sheets

FOREIGN PATENT DOCUMENTS

| WO | WO 96/32105 | 10/1996 |
|---|---|---|
| WO | WO 99/09006 | 2/1999 |
| WO | WO 99/15183 | 4/1999 |
| WO | WO 00/23614 | 4/2000 |
| WO | WO 02/47610 | 6/2002 |
| WO | WO 02/067901 | 9/2002 |
| WO | WO 2004/043374 A | 11/2003 |
| WO | WO 2004/071382 | 8/2004 |
| WO | WO 2005/002572 | 1/2005 |
| WO | WO 2005/003137 | 1/2005 |
| WO | WO 2006/028525 | 3/2005 |
| WO | WO 2005/094423 | 10/2005 |
| WO | WO 2005/099687 | 10/2005 |
| WO | WO 2006/005551 | 1/2006 |
| WO | WO 2006/017346 | 2/2006 |
| WO | WO 2006/060609 | 6/2006 |
| WO | WO 2006/060809 | 6/2006 |
| WO | WO 2006/118973 | 11/2006 |
| WO | WO 2007/021897 | 2/2007 |
| WO | WO 2007/033039 | 3/2007 |
| WO | WO 2007/138116 | 12/2007 |
| WO | WO 2008/137780 | 11/2008 |

OTHER PUBLICATIONS

Adams, Julian, "Proteasome Inhibitors as New Anticancer Drugs", *Curr. Opin. Oncol.*, (2002) 14:628.

Adams, et al., "Proteasome Inhibitors: A Novel Class of Potent and Effective Antitumor Agents", *Cancer Res.*, (1999) 59:2615.

Adams, J., "The Development of Novel Targeted Therapeutics for Treatment of Multiple Myeloma Research Roundtable", *Euro. J. Haematology*, (2003) 70:263-272.

Alessandri, et al., "Mobilization of Capillary Endothelium In Vitro Induced by Effectors of Angiogenesis In Vivo", *Cancer Res.*, (1983) 43(4):1790-1797.

Alm, et al., "Effects of Topically Applied PGF2 and its Isopropylester on Normal and Glaucomatous Human Eyes", *Prog. Clin. Biol. Res.*, (1989) 312:447-58.

Beers et al. (Eds.), *The Merck Manual of Diagnosis and Therapy*, 17th Ed. 1999, Merck & Co., pp. 397-398, 948-949, 1916 and 1979-1981.

Beers et al. (Eds.), *The Merck Manual of Diagnosis and Therapy*, 17th Ed. 1999, The Merck Research Laboratories, Whitehouse Station N.J., pp. 1193-1204. XP002510943.

Bernan, et al., "Marine Microorganisms as a Source of New Natural Products", *Advances in Applied Microbiology*, (1997) 43:57-90.

Bhalla, et al., "High-Dose Mitoxantrone Induces Programmed Cell Death or Apoptosis in Human Myeloid Leukemia Cells", *Blood*, (1993) 82(10):3133-3140.

Bicknell, et al. (Eds.), *Tumour Angiogenesis*, Oxford University Press, New York (1997), Table of Contents, pp. 5.

Blum, et al., "Adriamycin: A New Anticancer Drug with Significant Clinical Activity", *Ann Intern Med*, (1974) 80(2):249-259.

Blunt, et al., "Marine Natural Products", *Nat. Prod. Rep.*, (2003) 20:1-48.

Bodart, et al., "Anthrax, MEK and Cancer", *Cell Cycle*, (2002) 1:10-15.

Bradley, et al., "Identification of the Cellular Receptor for Anthrax Toxin", *Nature*, (2001) 414:225-229.

Bull, et al., "Search and Discovery Strategies for Biotechnology: the Paradigm Shift", *Microbiol. Mol. Biol. Rev.*, (2000) 64(3):573-606.

Carey, Francis, *Organic Chemistry*, 2nd ed., McGraw Hill, Inc., New York (1992), pp. 328-331.

Chauhan, et al., "A Novel Orally Active Proteasome Inhibitor Induces Apoptosis in Multiple Myeloma Cells with Mechanisms Distinct from Bortezomib", *Cancer Cell*, (2005) 8:407-419.

Chauhan, et al., "A Novel Proteasome Inhibitor NPI-0052 as an Anticancer Therapy," *British Journal of Cancer*, (2006) 95(8):961-965.

Cheng, et al., "Arenaric Acid, a New Pentacyclic Polyether Produced by a Marine Bacterium (Actinomycetales)", *J. Nat. Prod.*, (1999) 62:605-607.

Cheng, et al., "Luisols A and B, New Aromatic Tetraols Produced by an Estuarine Marine Bacterium of the Genus *Streptomyces* (Actinomycetales)", *J. Nat. Prod.*, (1999) 62:608-610.

Claverol, et al., "Mapping and Structural Dissection of Human 20 S Proteasome Using Proteomic Approaches", *Mol Cell Proteomics*, (2002) 1:567-78.

Colquhoun, et al, "Rapid Characterization of Deep-Sea Actionmycetes for Biotechnology Screening Programmes", *Antonie Van Leeuwenoek*, (2000) 77:359-367.

Colquhoun, et al., "Novel Rhodococci and Other Mycolate Actinomycetes From the Deep Sea", *Antonie van Leeuwenhoek*, (1998) 74:27-40.

Colquhoun, et al., "Taxonomy and Biotransformation Activites of Some Deep-Sea Actinomycetes", *Extremophiles*, (1998) 2:269-277.

Corey et al. "The Structural Requirements for Inhibition of Proteasome Function by the Lactacystin-derived beta-lactone and Synthetic Analogs", *Tetrahedron* (1999) 55(11):3305-3316.

Crane, et al., "A Novel Enantioselective Synthetic Route to Omuralide Analogues with the Potential for Species Selectivity in Proteasome Inhibition", *Organic Letters*, (2001) 1395-1397.

Cragg, et al. "Chemical Diversity: A Function of Biodiversity", *Trends Pharmacol. Sci.*, (2002) 23:404.

Crueger, et al. (Eds.), *Biotechnology: A Textbook of Industrial Microbiology*, 2nd ed. (English Edition, Thomas D. Brock Ed.), Sinauer Associates Inc, Sunderland MA, (1990) Chapter 2:4-8.

Cusack, et al., "Enhanced Chemosensitivity to CPT-11 with Proteasome Inhibitor PS-341: Implications for Systemic Nuclear Factor-kB Inhibition", *Cancer Res.*, (2001) 61:3535-3564.

Cusack, et al., NPI-0052 Enhances Tumoricidal Response to Conventional Cancer Therapy in a Colon Cancer Model, *Clin Cancer Res.*, (2006) 22:6758-6764.

Davidson, Bradley S., "New Dimensions in Natural Products Research: Cultured Marine Microorganisms", *Current Opinion in Biotechnology*, (1995) 6:284-291.

Decker, et al., "Inhibition of Caspase-3-mediated Poly (ADP-ribose) Polymerase (PARP) Apoptotic Cleavage by Human PARP Autoantibodies and Effect on Cells Undergoing Apoptosis", *J. Biol. Chem.*, (2000) 275(12):9043-9046.

Delong, et al. "Environmental Diversity of Bacteria and Archaea", *Syst. Biol.*, (2001) 50(4):470-478.

Dick, et al., "Mechanistic Studies on the Inactivation of the Proteasome by Lactacystin", *J. Biol. Chem.*, (1996) 271(13):7273-7276.

"DTP Human Tumor Cell Line Screen." Screening Services. DPI. Sep. 28, 2005 http://dtp.nci.nih.gov/branches/btb/ivclsp.html.

Duesbery, et al., "Proteolytic Inactivation of MAP-Kinase-Kinase by Anthrax Lethal Factor", *Science*, (1998) 280:734-737.

Elliott, et al., "Proteasome Inhibition: A New Anti-Inflammatory Strategy", *J. Mol. Med.*, (2003) 81:235-245.

Elliot, et al., "The Proteasome: A New Target for Novel Drug Therapies", *American Journal of Clinical Pathology*, (2001) 637-646.

Endo, et al., "Total Synthesis of Salinosporamide A", *J. Am. Chem. Soc.*, (2005) 127(23): 8298-8299 and Supporting Information S1-S23.

Erba, et al., "Mode of Action of Thiocoraline: A Natural Marine Compound With Anti-Tumor Activity", *British Journal of Cancer*, (1999) 88(7):971-980.

Escuyer, et al., "Anthrax Protective Antigen Interacts with a Specific Receptor on the Surface of CHO-K1 Cells", *Infect. Immun.*, (1991) 59(10):3381-3386.

Faulkner, D. John, "Marine Natural Products", *Nat. Prod. Rep.*, (2001) 18(1):1-49.

Feling, et al. "Salinosporamide A: A Highly Cytotoxic Proteasome Inhibitor from a Novel Microbial Source, a Marine Bacterium of the New Genus *Salinospora*", *Angew. Chem. Int. Ed.*, (2003) 42(3):355-357.

Fenical, et al., "Marine Microorganisms as a Developing Resource for Drug Discovery", *Pharmaceutical News*, (2002) 489-494.

Fenical, et al., "Marine Microorganisms as a Biomedical Source: Are They Unculturable or Uncultured?", PowerPoint Presentation, Center for Marine Biotechnology and Biomedicine (Feb. 24, 2002).

Fenical, et al., "Marine Microorganisms as a Developing Resource for Drug Discovery", *Pharmaceutical News*, (2002) 9:489-494.
Fenical, et al., "*Salinospora*, a Major New Marine Actinomycete Taxon for Drug Discovey", Powerpoint Presentation, Center for Marine Biotechnology and Biomedicine (Jun. 24, 2001).
Fenical, William, "Chemical Studies of Marine Bacteria: Developing a New Resource", *Chem. Rev.*, (1993) 93(5):1673-1683.
Fenical, William, "New Pharmaceuticals From Marine Organisms", *Marine Biotechnology*, (1997) 15:339-341.
Fenteany, et al., "Inhibition of Proteasome Activities and Subunit-Specific Amino-Terminal Threonine modification by Lactacystin", *Science*, (1995) 268:726-731.
Fenteany, et al., "Lactacystin, Proteasome Function, and Cell Fate," *J. Biol. Chem.* (1998) 273(15): 8545-8548.
Fernandez-Chimeno, et al., "IB-96212, a Novel Cytotoxic Macrolide Produced by a Marine *Micromonospora*", *Journal of Antibiotics*, (2000) 53(5):474-478.
Fingl, et al., "General Principals," *The Pharmaceutical Basis of Therapeutics*, 5th Ed., (Goodman et al. Eds., 1975), MacMillan Publishing Co. Inc., New York, Chapter 1: 1-46.
Folkman, Judah, "Tumor Angiogenesis", *Adv Cancer Res.*, (1985) 43:175-203.
Folkman, Judah, "Angiogenesis-Dependent Diseases", *Seminars in Oncology*, (Dec. 2001) 28:536-542.
Fukuchi, et al., "Direct proteasome inhibiton by *clasto*-lactacystin β-lactone permits the detection of ubiquitinated p21 in ML-1 Cells", *Biochem. Biophys. Acta*, (1999) 1451:206-210.
Fusetani, Nobuhiro, "Marine Microorganisms and Drug Discovery: Current Status and Future Potential," *Drugs from the Sea*, (2000), 6-29.
Gale, et al. (Eds.), *The Molecular Basis of Antibiotic Action*, 2nd ed., John Wiley and Sons, London (1981) Table of Contents, pp. 1-13.
Gantt, et al., "Proteasome Inhibitors Block Development of Plasmodium SPP", *Antimicrobial Agents and Chemotherapy*, (1998) 2731-2738.
Geier, et al., "A Giant Protease with Potential to Substitute for Some Functions of the Proteasome", *Science*, (1999) 283:978-981.
Giannangeli et al., "Effect of Modifications of the Alkylpiperazine Moiety of Trazodone on $5HT_{2A}$ and $a_1$ Receptor Binding Affinity", *J. Med. Chem.*, (1999) 42(3):336-356.
Giovannoni, Stephen, "Oceans of Bacteria", *Nature*, (Jul. 29, 2004) 430:515-516.
Goldberg, et al., "Not Just Research Tools—Proteasome Inhibitors Offer Therapeutic Promise", *Natural Medicine*, (2002) 338-340.
Golub, et al., "Molecular Classification of Cancer; Class Discovery and Class Prediction by Gene Expression Monitoring", *Science*, (1999) 286:531-537.
Goodfellow, et al., "Actinomycetes in Biotechnology," *Search and Discovery of New Antibiotics*, Okami, et al., eds., Academic Press, San Diego, (1988) Chapter 2:33-67.
Goodfellow, et al., "Actinomycetes in Marine Sediments", *Biological Biochemical and Biomedical Aspects of Actinomycetes*, Ortiz-Ortiz, et al., eds., Academic Press, Inc., Orlando (1984) 453-472.
Goodfellow, et al., "Ecology of Actinomycestes", *Ann. Rev. Microbiol.*, (1983) 37:189-216.
Goodfellow, et al., "Search and Discovery of Industrially Significant Actinomycetes", *Microbial Products: New Approaches, Society for General Microbiology Symposium*, (1989) 44:343-383.
Grant, et al., "Intracellular Mechanisms Involved in Basement Membrane Induced Blood Vessel Differentiation In Vitro", *In Vitro Cell Dev. Biol.*, (1991) 27A:327-336.
Grosios, et al., "Angiogenesis Inhibition by the Novel VEGF Receptor Tyrosine Kinase Inhibitor; PTK787/ZK222584, Causes Significant Anti-Arthritic Effects in Models of Rheumatoid Arthritis", *Inflamm Res*, (2004) 53: 133-142.
Hanna, et al., "On the Role of Macrophages in Anthrax", *Proc Natl Acad Sci USA*, (1993) 90:10198-10201.
Hardt, et al., "Neomarinone, and New Cytotoxic Marinone Derivatives, Produced by a Marine Filamentous Bacterium (Actinomycetales)", *Tetrahedron Letters*, (2000) 41(13):2073-2076.
Harker, et al., "Multidrug Resistance in Mitoxantrone-Selected HL-60 Leukemia Cells in the Absence of P-Glycoprotein Overexpression", *Cancer Res.*, (1989) 15:4542-4549.

Haustedt et al., "Rational approaches to natural-product-based drug design," *Curr. Opin. Drug Discovery Dev.*, (2006) 9(4): 445-462.
He, et al., "*Lomaiviticins A and B, Potent Antitumor Antibiotics from Micromonospora lomaivitiensis*", *J. Am. Chem. Soc.*, (2001) 123(22):5362-5363.
Helmke, et al., "Rhodococcus *Marinonascens* sp. nov.: An Actinomycete From the Sea", *International J. of Systematic Bacteriology*, (Apr. 1984) 34(2):127-128.
Hideshima, et al., "NF-κB as a Therapeutic Target in Multiple Myeloma," *J. Biol. Chem.*, (2002) 277(19):16639-16647.
Higuchi, et al., "Pro-Drugs as Novel Delivery Systems", vol. 14, A.C.S. Symposium Series *American Chemical Society*, Atlantic City, NJ., Sep. 10, 1974, (1975) Table of Contents, pp. 3.
Hopwood, et al., "Genetic Manipulation of *Streptomyces* Polyketide Synthase Genes for Novel Secondary Metabolite Production," *FEMA Microbiology Reviews*, (1995) 16:233-234.
Horan, Ann C., "Aerobic Actinomycetes: A Continuing Source of Novel Natural Products," *The Discovery of Natural Products with Therapeutic Potential (Biotechnology)*, Vincent P. Gullo (Ed.), Butterworth-Heinemann, Boston (1994) Chapter 1: 1-30.
Hull, et al., "Antiangiogenic Agents Are Effective Inhibitors of Endometriosis," *J. Clinical Endocrinology Metabolism*, (2003) 88:2889-2899.
Jensen, et al., "Strategies for the Discovery of Secondary Metabolites from Marine Bacteria: Ecological Perspectives", *Annu. Rev. Microbiology*, (1994) 48:559-584.
Jensen, et al., "Distribution of Actinomycetes in Near-Shore Tropical Marine Sediments", *Applied and Environmental Microbiology*, (Apr. 1991) 57(4):1102-1108.
Jensen, et al., "Marine Microorganisms and Drug Discovery: Current Status and Future Potential", *Drugs from the Sea*, Nobuhiro Fusetani Ed., Krager, Basel Switzerland (2000) 6-29.
Jensen, et al., "The Relative Abundance and Seawater Requirements of Gram-Positive Bacteria in Near-Shore Tropical Marine Samples", *Microbial Ecology*, (1995) 29(3):249-257.
Jiang, et al., "Antinoflavoside, A Novel Flavonoid-Like Glycoside Produced by a Marine Bacterium of the Genus *Streptomyces*", *Tetrahedron Letters*, (1997) 38(29):5065-5068.
Joseph, et al., "Laboratory Cultivation of Widespread and Previously Uncultured Soil Bacteria", *Applied and Environmental Microbiology*, (2003) 69(12):7210-7215.
Joshi, A., "Microparticulates for Ophthalmic Drug Delivery", *J. Ocul. Pharmacol.*, (1994) 10:29-45.
Kalns, et al., "TNF Receptor 1, IL-1 Receptor, and iNOS Genetic Knockout Mice Are Not Protected from Anthrax Infection", *Biochem. Biophys. Res. Commun.*, (2002) 292:41-44.
Kalns, et al., "Delayed Treatment With Doxycycline Has Limited Effect on Anthrax Infection in BLK57/B6 Mice", *Biochem. Biophys. Res. Commun.*, (2002) 297:506-509.
Kerr, et al., "Marine Natural Products as Therapeutic Agents", *Exp. Opinion on Therapeutic Patents*, (1999) 9:1207-1223.
Kim, et al., "Sensitizing Anthrax Lethal Toxin-Resistant Macrophages to Lethal Toxin-Induced Killing by Tumor Necrosis Factor", *J. Biol. Chem.*, (2003) 278:7413-7421.
King, et al., "How Proteolysis Drives the Cell Cycle", *Science*, (1996) 274:1652-1659.
Kisselev, et al., "Proteasome Inhibitors: From Research Tools to Drug Candidates", *Chem. Biol.*, (2001) 8:739-758.
Koch, et al., "16S Ribosomal DNA Analysis of The Genera *Micromonospora, Actinoplanes, Catellatospora, Catenuloplanes, Dactylosporangium, and Pillimelia* and Emendation or the Family *Micromonosporaceae*", *Intl Journal of Systematic Bacteriology*, (Jul. 1996) 46(3):765-768.
Kozlowski, et al., "Lactacystin Inhibits Cathepsin A Activity in Melanoma Cell Lines", *Tumor Biol.*, (2001) 22:211-215.
Lacy, et al., "Mapping the Anthrax Protective Antigen Binding Site on the Lethal and Edema Factors", *J. Biol. Chem.*, (2002) 277:3006-3011.
Lam, et al., "Isolation of a Bromo Analog of Rebeccamycin From *Saccharothrix aerocolonigenes*", *J. Antibiotics*, (Sep. 1991) 44(9):934-939.

Lam, et al., "Production, Isolation and Structure Determination of Novel Fluoroindolocarbazoles from *Saccharothrix aerocolonigenes* ATCC 39243", *J. Antibiotics*, (2001) 54(1):1-9.

Lawley, et al., "Induction of Morphologic Differentiation of Endothelial Cells in Culture", *J. Investigative Dermatology*, (Aug. 1989) 93(2 Supplement):59S-61S.

Lightcap, et al., "Proteasome Inhibition Measurements Clinical Application", *Clin. Chem.*, (2000) 46(5):673-683.

Lin, et al., "Cytotoxic Effects of Anthrax Lethal Toxin on Macrophage-Like Cell Line J774A.1", *Curr. Microbiol.*, (1996) 33:224-227.

Liu, et al., "Precursor Supply for Polyketide Biosynthesis: The Role of Crotonyl-CoA Reductase", *Metab. Eng.*, (2001) 3:40-48.

Liu, et al., "Angiogenesis Inhibitors May Regulate Adiposity", *Nutr. Rev.*, (2003) 61:384-387.

Macherla, et al., "Structure-Activity Relationship Studies of Salinosporamide A (NPI-0052), a Novel Marine Derived Proteasome Inhibitor", *J. Med. Chem.*, (2005) 48(11): 3684-3687.

Mayer, et al., "Efficacy of a Novel Hydrogel Formulation in Human Volunteers", *Ophthalmologica*, (1996) 210(2):101-103.

Mayer, et al., "Marine Pharmacology in 1999: Antitumor and Cytotoxic Compounds." *Anticancer Res.*, (2001) 21:2489-2500.

McMurry, John, *Organic Chemistry*, 5th ed., Brooks/Cole, Pacific Grove, CA. (2000), pp. 398-408.

Meng, et al., "Eponemycin Exerts its Antitumor Effect Through the Inhibition of Proteasome Function," *Cancer Res.*, (1999), 59(12):2798-2801.

Meng, et al., "Epoxomicin, a Potent and Selective Proteasome Inhibitor, Exhibits In Vivo Anti-Inflammatory Activity", *Proc. Natl. Acad. Sci.*, (Aug. 1999) 96:10403-10408.

Min, et al., "Urokinase Receptor Antagonists Inhibit Angiogenesis and Primary Tumor Growth in Syngeneic Mice", *Cancer Res.*, (May 15, 1996) 56(10):2428-2433.

Mincer, et al., "Widespread and Persistent Populations of a Major New Marine Actinomycete Taxon in Ocean Sediments", *Applied and Environmental Microbiology*, (Oct. 2002) 68(10):5005-5011.

Mogridge, et al., "Stoichiometry of Anthrax Toxin Complexes", *Biochemistry*, (2002) 41:1079-1082.

Moore, B.S., "Biosynthesis of Marine Natural Products: Microorganisms and Macroalgae", *Nat. Prod. Rep.*, (1999) 16(6):653-674.

Mordenti, et al., "Intracular Pharmacokinetics and Safety of a Humanized Monoclonal Antibody in Rabbits after Intravitreal Administration of a Solution or a PLGA Microsphere Formulation", *Toxicol. Sci.*, (1999) 52(1):101-106.

Moran, et al., "Evidence for Indigenous Streptomyces Populations in Marine Environment Determined with a 16S rRNA Probe," *Applied and Environmental Microbiology*, (Oct. 1995) 61(10):3695-3700.

Mousa, et al., "Angiogenesis Inhibitors: Current & Future Directions", *Current Pharmaceutical Design*, (2004) 10:1-9.

Mulholland et al., "A Concise Total Synthesis of Salinosporamide A," *Org. Biomol. Chem.*, (2006) 4: 2845-6.

Murray, J. Clifford (Ed.), *Angiogenesis Protocols (Methods in Molecular Medicine)*, Humana Press, Totowa, NJ. (2001) Table of Contents, p. 4.

NCBI website, sequence for EF105548, http://www.ncbi.nlm.nih.gov/entrez/viewer.fcgi?db=nucleotide&val=118640518, 2 pages, downloaded Feb. 15, 2007, 2 pages.

NCBI website, sequence for AB242910, http://www.ncbi.nlm.nih.gov/entrez/viewer.fcgi?db=nucleotide&val=124300751, 2 pages, downloaded Feb. 15, 2007, 2 pages.

NCBI website, Sequence for EF191171, http://www.ncbi.nlm.nih.gov/entrez/viewer.fcgi?db=nucleotide&val=124014014, 2 Pages, downloaded Feb. 15, 2007, 2 pages.

Nesterneko, et al., "*Rhodococcus luteus* nom. nov., and *Rhodococcus maris* nom. nov.", *Int'l Journal of Systematic Bacteriology*, (Jan. 1982) 32(1):1-14.

Newton. "Il fondo agli oceani potenti antibiotici e anticancro." www.newton.rcs.it/PrimoPiano/News/2003/02_Febbraio/03/Antobiotico.html. (Feb. 2, 2003) 1 page. XP002304843.

Nicholson, D.W., "ICE/CED 3-Like Proteases as Therapeutic Targets for the Control of Inappropriate Apoptosis", *Nat. Biotechnology*, (1996) 14:297-301.

Nicosia, et al., "Growth of Microvessels in Serum-Free Matrix Culture of Rat Aorta: A Quantitative Assay of Angiogenesis In Vitro," *Laboratory Investigation*, (Jul. 1990) 63(1):115-122.

Nicolaus B.J. R. "Symbiotic Approach to Drug Design", *Decision Making in Drug Research*, (1983) 173-189. XP002197412.

Nolan, et al., "Isolation and Screening of Actinomycetes", *Actinomycetes in Biotechnology*, (1988) Chapter 1:1-32.

O'Donnel, Anthony G., "Recognition of Novel Actinomycetes", *Actinomycetes in Biotechnology*, Academic Press, (1988) Chapter 3:69-88.

Olkawa, et al., "Angiogenic Factor of a Rat Mammary Tumor Cell Line (RMT-1) (I). Secretion of Two Distinct Angiogenic Factors into Serum-Free Conditioned Medium by RMT-1 Cells", *Cancer Letters*, (1991) 59:57-66.

Okami, Y., "The Search for Bioactive Metabolites from Marine Bacteria", *J. Marine Biotechnology*, (1993) 1:59-65.

Omura, et al., "Lactacystin, A Novel Microbial Metabolite, Induces Neuritogenesis of Neuroblastoma Cells," *J. Antibiotics*, (1991) 44(1): 113-116.

O'Neil et al. eds., "The Merck Index," 13th Ed. 2001, Merck Research Laboratories, Whitehouse Station N.J., pp. THER-5-THER-7. XP002510887.

Ostrowska, et al., "Lactacystin, A Specific Inhibitor of the Proteasome, Inhibits Human Platelet Lysosomal Cathepsin A-like Enzyme." *Biochem. Biophys. Res. Commun.*, (1997) 234:729-732.

Ostrowska, et al., "Separation of Cathepsin A-like Enzyme and the Proteasome: Evidence that Lactacystin/β-Lactone is not a Specific Inhibitor of the Proteasome", *Int. J. Biochem. Cell Biol.*, (2000) 32:747-757.

Otoguro, et al., "An intergrated method for the enrichment and selective isolation of *Actinokineospora* spp. in soil and plant litter," *J. Appl. Microbiol.*, (2001) 92:118-130.

Peckham et al. (Eds.), "The Oxford Textbook of Oncology", *Oxford University Press*, Oxford (1995) vol. 1:447-453.

Pagano, et al., "Role of the Ubiquitin-Proteasome Pathway in Regulating Abundance of the Cyclin-Dependent Kinase Inhibitor p27," *Science*, (1995) 269(5224):682-685.

Page, Roderic D.M., "TreeView: An Application to Display Phylogenetic Trees on Personal Computers", *Computer Applications in the Biosciences*, (1996) 12:357-358.

Painter, Robert B., "Inhibition of DNA Replicon Initiation by 4-Nitroquinoline 1-Oxide, Adriamycin, and Ethyleneimine", *Cancer Res.*, (1978) 38(12):4445-4449.

Palayoor, et al., "Constitutive Activation of IκB Kinase α and NF-κB in Prostate Cancer Cells is Inhibited by Ibuprofen", *Oncogene*, (1999) 18:7389-7394.

Plunkett, et al., "Methods in Laboratory Investigation: An In Vivo Quantitative Angiogenesis Model Using Tumor Cells Entrapped in Alginate", *Laboratory Investigation*, (Apr. 1990) 62(4):510-517.

Prudhomme et al., "Marine Actinomycetes: A New Source of Compounds against the Human Malaria Parasite," Plos One, (2008) 3(6): 1-8. XP008100452.

Qureshi, et al., "The Proteasome as a Libopolysaccharide-Binding Protein in Macrophages: Differential Effects of Proteasome Inhibition on Lipopolysaccharide-Induced Signaling Events," *J. Immunol.*, (2003) 171(3):1515-1525.

Rappe, et al., "Cultivation of the Ubiquitous SAR11 Marine Bacterioplankton Clade", *Nature*, (Aug. 8, 2002) 418:630-633.

Reddy, et al., "A Simple Stereocontrolled Synthesis of Salinosporamide A", *J. Am. Chem. Soc.*, (2004) 126(20):6230-6231. XP008038141.

Alfonso R. Gennaro (Ed.), *Remington's Pharmaceutical Sciences*, 17th Ed., Mack Publishing Co., Easton, PA, (1985), Table of Contents, pp. 5.

Alfonso R. Gennaro (Ed.), *Remington's Pharmaceutical Sciences*, 18th Ed., Mack Publishing Co., Easton, PA (1990), Table of Contents, pp. 5.

Riva, S., "Biocatalytic Modification of Natural Products," *Curr. Opin. Chem. Biol.*, (2001) 5:106-111.

Edward B. Roche (Ed.),. "Bioreversible Carriers in Drug Design: Theory and Application", Pergamon Press, Elmsford, NY (1987), pp. 14-21.

Romero, et al., "Thiocoraline, a New Depsipeptide with Antitumor Activity Produced by a Marine *Micromonospora*", *The Journal of Antibiotics*, (1997) 50(9):734-737.

Gabor M. Rubanyi (Ed.), "Angiogenesis in Health and Disease: Basic Mechanisms and Clinical Applications", Marcel Dekker, New York, NY (1999) Table of Contents, p. 6.

Ruiz, et al., The Proteasome Inhibitor NPI-0052 is a More Effective Inducer of Apoptosis than Bortezomib in Lymphocytes from Patients with Chronic Lymphocytic Leukemia, *Mol. Cancer Ther*., (2006) 5(7): 1836-1843.

Sapi, et al., "Simple And Condensed beta-Lactams . . . ". *Collection of Czechoslovak Chemical Communications* (1999) 64(2):190-202.

Schnaper, et al., "Plasminogen Activators Augment Endothelial Cell Organization In Vitro by Two Distinct Pathways", *J. Cell. Physiol*., (1995) 165:107-118.

Shadomy, et al., "Antimycotic and Antirickettsial," *Antibiotics, Chemotherapeutics, and Antibacterial Agents for Disease Control*, Martin Grayson (Ed.) John Wiley and Sons, New York (1982) 371-395.

Shah, et al., "Early Clinical Experience With the Novel Proteasome Inhibitor PS-519", *J. Clin. Pharmacol*., (2002) 54:269-276.

Shedden, et al., "Efficacy and Tolerability of Timolol Maleate Ophthalmic Gel-Forming Solution Versus Timolol Ophthalmic Solution in Adults with Open-Angle Glaucoma or Ocular Hypertension: A Six-Month, Double Masked, Multicenter Study", *Clin. Ther*., (2001) 23(3):440-450.

Shimada, et al., "Contributions of Mitogen-Activated Protein Kinase and Nuclear Factor Kappa B to N-(4-hydroxyphenyl) Retinamide-Induced Apoptosis in Prostate Cancer Cells", *Molecular Carcinogenesis*, (2002) 35(3):127-137.

Silverman, Richard B., *The Organic Chemistry of Drug Design and Drug Action*, Academic Press, San Diego, (1992) 19-21.

Stach, et al., "Statistical Approaches for Estimating Actinobacterial Diversity in Marine Sediments", *Applied and Environmental Microbiology*, (Oct. 2003) 69(10):6189-6200.

Stach, et al., "New Primers for the Class *Actinobacteria*: Application to Marine and Terrestrial Environments", *Applied and Environmental Mircrobiology*, (2003) 5(10):828-841.

Stackebrandt, et al., "Proposal for a New Hierarchic Classification Systems, *Actinobacteria* classis Nov.," *Int'l Journal of Systematic Bacteriology*, (Apr. 1997) 47:479-491.

Stackebrandt, et al., "Taxonomic Note: A Place for DNA-DNA Reassociation and 16S rRNA Sequence Analysis in the Present Species Definition in Bacteriology", *Int. J. of Syst. Bacteriol*., (1994) 44(4):846-849.

Stadler et al., "Cinnabaramides A-G: Analogues of Lactacystin and Salinosporamide from a Terrestrial Streptomycete," *J. Nat. Prod*. (Feb. 2007) 70(2):246-252.

Stanford, et al., "Bortezomib Treatment for Multiple Myeloma", *The Ann. of Pharma*., (2003) 37:1825-1830.

Streitwieser et al., *Introduction to Organic Chemistry*, 2nd ed., Macmillan Publishing Co. Inc., New York, NY (1981) pp. 169-171.

Sunwoo, et al., "Novel Proteasome Inhibitor PS-341 Inhibits Activation of Nuclear Factor-kB, Cell Survival, Tumor Growth, and Angiogenesis in Squamous Cell Carcinoma", *Clin. Cancer Res*., (2001) 7:1419-1428.

Takeuchi, et al., "Troglitazone Induces G1 Arrest by p27 Induction That Is Mediated by Inhibition of Proteasome in Human Gastric Cancer Cells", *Jpn. J. Cancer Res*., (2002) 93:774-782.

Tang, et al., "Proteasome Activity is Required for Anthrax Lethal Toxin to Kill Macrophages", *Infection and Immunity*, (1999) 67:3055-3060.

Tang, et al., "Cloning and Hererologous Expression of the Epothilong Gene Cluster", *Science*, (Jan. 28, 2000) 287:640-642.

Tauchi, et al., "Molecular Mechanisms of Resistance of Leukemia to Imatinib Mesylate", *Leukemia Research*, (May 2004) 28:39-45.

Thompson, et al., "CLUSTAL W: improving the sensitivity of progressive multiple sequence alignment through sequence weighting, position-specific gap penalties and weight matrix choice", *Nucleic Acids Research*, (1994) 22:4673-4680.

Versalovic, et al., "Distribution of repetitive DNA sequences in eubacteria and application to fingerprinting of bacterial genomes," *Nucleic Acids Research*, (1991) 19(24):6823-6831.

Vitale, et al., "Susceptibility of Mitogen-Activated Protein Kinase Kinase Family Members to Proteolysis by Anthrax Lethal Factor", *Biochem. J*., (2000) 352:739-745.

Vitale, et al., "Anthrax lethal factor cleaves the N-terminus of MAPKKS and induces tyrosine/threonine phosphorylation of MAPKS in cultured macrophages," *J. Applied Microbiology*, (1999) 87:288.

Ward, Bess B., "How Many Species of Prokaryotes are There?", *PNAS*, (Aug. 6, 2002) 99(16):10234-10236.

Watve, et al., "How Many Antibiotics Are Produced by the Genus *Streptomyces*?", *Arch. Microbio*., (2001) 176:386-390.

Weyland, H., "Actinomycetes in North Sea and Atlantic Ocean Sediments", *Nature*, (1969) 223:858.

Weyland, H., "Distribution of Actinomycetes on the Sea Floor", *Actinomycestes ZBL*. Bakt. Suppl., (1981) 11:185-193.

Wheelis, et al., "On the Nature of Global Classification", *PNAS*, (Apr. 1992) 89:2930-2934.

Williams et al., "New Cytotoix Salinosporamides Form the Marine Actinomycete Salinispora Tropica", *J. Org. Chem*., (2005) 70(16):6196-6203.

Woese, Carl R., "Bacterial Evolution", *Microbiological Rev*., (Jun. 1987) 51(2):221-271.

Zaks, A., "Industrial Biocatalysis", *Curr. Opin. Chem. Biol*., (2001) 5:130-136.

Zhang, et al., "Postischemic (6 Hour) Treatment with Recombinant Human Tissue Plaminogen Activator and Proteasome Inhibitor PS-519 Reduces Infarction in a Rat Model of Embolic Focal Cerebral Ischemia", *Stroke*, (2001) 2926-2931.

Zheng, et al., "Detection of Antitumor and Antimicrobial Activities in Marine Organism Associated Actinomycetes Isolated From the Taiwan Strait, China", *FEMS Microbiology Letters*, (2000) 188:87-91.

International Search Report and Written Opinion dated Jul. 12, 2006 in International Application No. PCT/US2005/044091, International Filing Date: Dec. 2, 2005.

International Preliminary Report on Patentability dated Jun. 14, 2007 in International Application No. PCT/US2005/044091, International Filing Date: Dec. 2, 2005.

International Search Report and Written Opinion (corrected version) dated Jul. 8, 2005 in International Application No. PCT/US2004/019543, International Filing Date: Jun. 18, 2004.

International Preliminary Report on Patentability dated Jan. 3, 2006 in International Application No. PCT/US2004/019543, International Filing Date Jun. 18, 2004.

International Preliminary Report on Patentability dated Mar. 14, 2005 in International Application No. PCT/US2004/019453, International Filing Date: Jun. 18, 2004.

Written Opinion dated Nov. 29, 2004 in International Application No. PCT/US2004/019453, International Filing Date: Jun. 18, 2004.

International Search Report and Written Opinion dated Dec. 29, 2006 in International Application No. PCT/US2005/014846, International Filing Date: Apr. 29, 2005.

International Preliminary Report on Patentability dated Jan. 23, 2007 in International Application No. PCT/US2005/014846, International Filing Date: Apr. 29, 2005.

International Search Report dated Aug. 2, 2002 in International Application No. PCT/US01/043758, International Filing Date Nov. 16, 2001.

International Preliminary Report on Patentability dated Sep. 1, 2004 in International Application No. PCT/US2001/043758, International Filing Date: Nov. 16, 2001.

International Search Report and Written Opinion dated Feb. 27, 2007 in International Application No. PCT/US06/016104, International Filing Date Apr. 27, 2006.

International Preliminary Report on Patentability dated Oct. 30, 2007 in International Application No. PCT/US2006/016104, International Filing Date Apr. 27, 2006.

International Search Report and Written Opinion mailed Jan. 5, 2009 for corresponding PCT Application No. PCT/US2008/052956 filed Apr. 2, 2008.

International Search Report and Written Opinion mailed Jan. 29, 2009 for corresponding PCT Application No. PCT/US2008/062553 filed May 2, 2008.

Notice of Allowance in U.S. Appl. No. 10/838,157, Dated May 15, 2006.
Office Action in U.S. Appl. No. 10/871,368, Dated Nov. 1, 2006.
Office Action in U.S. Appl. No. 10/871,368, Dated May 15, 2007.
Office Action in U.S. Appl. No. 10/871,368, Dated Sep. 19, 2007.
Office Action in U.S. Appl. No. 10/871,368, Dated Mar. 10, 2008.
Office Action in U.S. Appl. No. 11/118,260, Dated Oct. 30, 2006.
Notice of Allowance in U.S. Appl. No. 11/118,260, Dated Apr. 24, 2007.
Office Action in U.S. Appl. No. 11/228,416, Dated Feb. 21, 2007.
Advisory Action in U.S. Appl. No. 09/991,518, Dated Mar. 7, 2006.
Office Action in U.S. Appl. No. 09/991,518, Dated Sep. 15, 2003.
Office Action in U.S. Appl. No. 09/991,518, Dated Feb. 24, 2004.
Office Action in U.S. Appl. No. 09/991,518, Dated Aug. 20, 2004.
Office Action in U.S. Appl. No. 09/991,518, Dated Feb. 15, 2005.
Office Action in U.S. Appl. No. 09/991,518, Dated Jun. 27, 2005.
Office Action in U.S. Appl. No. 09/991,518, Dated Nov. 4, 2005.
Notice of Allowance in U.S. Appl. No. 09/991,518, Dated Apr. 24, 2006.
Office Action in U.S. Appl. No. 10/600,854, Dated Dec. 30, 2004.
Office Action in U.S. Appl. No. 10/600,854, Dated Aug. 19, 2005.
Notice of Allowance in U.S. Appl. No. 10/600,854, Dated May 15, 2006.
Notice of Allowance in U.S. Appl. No. 10/600,854, Dated Sep. 28, 2006.
Office Action in U.S. Appl. No. 10/838,157, Dated Aug. 19, 2005.
Notice of Allowance in U.S. Appl. No. 10/838,157, Dated Sep. 28, 2006.
Office Action in U.S. Appl. No. 11/147,622, Dated Dec. 2, 2005.
Notice of Allowance in U.S. Appl. No. 11/147,622, Dated Jun. 1, 2006.
Notice of Allowance in U.S. Appl. No. 11/147,622, Dated Sep. 29, 2006.
Office Action in U.S. Appl. No. 11/705,694, Dated Oct. 5, 2007.
Office Action in U.S. Appl. No. 11/705,694, Dated Jul. 21, 2008.
Advisory Action in U.S. Appl. No. 11/705,694, Dated Oct. 8, 2008.
Office Action in U.S. Appl. No. 11/705,694, Dated Dec. 29, 2008.
Office Action in U.S. Appl. No. 11/412,476, Dated Jul. 11, 2008.
Office Action in U.S. Appl. No. 11/453,374, Dated Jul. 14, 2008.
Office Action in U.S. Appl. No. 11/841,588, Dated Jan. 7, 2009.
Office Action in U.S. Appl. No. 11/453,374, Dated Jan. 12, 2009.
U.S. Appl. No. 11/966,801, filed Dec. 28, 2007.

* cited by examiner

LYOPHILIZED FORMULATIONS OF SALINOSPORAMIDE A

CROSS-REFERENCE TO RELATED APPLICATIONS

This application claims the benefit under 35 U.S.C. §119 (e) of U.S. provisional application Ser. No. 60/888,025, filed on Feb. 2, 2007, and U.S. provisional application Ser. No. 60/986,891, filed on Nov. 9, 2007, the disclosures of which are hereby expressly incorporated by reference in their entirety and are hereby made a portion of this application.

FIELD OF THE INVENTION

In some embodiments, the present invention relates to lyophilized formulations of Salinosporamide A.

BACKGROUND OF THE INVENTION

Cancer is a leading cause of death in the United States. Despite significant efforts to find new approaches for treating cancer, the primary treatment options remain surgery, chemotherapy and radiation therapy, either alone or in combination. Surgery and radiation therapy, however, are generally useful only for fairly defined types of cancer, and are of limited use for treating patients with disseminated disease. Chemotherapy is the method that is generally useful in treating patients with metastatic cancer or diffuse cancers such as leukemias. Although chemotherapy can provide a therapeutic benefit, it often fails to result in cure of the disease due to the patient's cancer cells becoming resistant to the chemotherapeutic agent. Due, in part, to the likelihood of cancer cells becoming resistant to a chemotherapeutic agent, such agents are commonly used in combination to treat patients.

Similarly, infectious diseases caused, for example, by bacteria, fungi and protozoa are becoming increasingly difficult to treat and cure. For example, more and more bacteria, fungi and protozoa are developing resistance to current antibiotics and chemotherapeutic agents. Examples of such microbes include *Bacillus, Leishmania, Plasmodium* and *Trypanosoma*.

Furthermore, a growing number of diseases and medical conditions are classified as inflammatory diseases. Such diseases include conditions such as asthma to cardiovascular diseases. These diseases continue to affect larger and larger numbers of people worldwide despite new therapies and medical advances.

Therefore, a need exists for additional chemotherapeutics, anti-microbial agents, and anti-inflammatory agents to treat cancer, inflammatory diseases and infectious disease. A continuing effort is being made by individual investigators, academia and companies to identify new, potentially useful chemotherapeutic and anti-microbial agents.

Marine-derived natural products are a rich source of potential new anti-cancer agents and anti-microbial agents. The oceans are massively complex and house a diverse assemblage of microbes that occur in environments of extreme variations in pressure, salinity, and temperature. Marine microorganisms have therefore developed unique metabolic and physiological capabilities that not only ensure survival in extreme and varied habitats, but also offer the potential to produce metabolites that would not be observed from terrestrial microorganisms (Okami, Y. 1993 *J Mar Biotechnol* 1:59). Representative structural classes of such metabolites include terpenes, peptides, polyketides, and compounds with mixed biosynthetic origins. Many of these molecules have demonstrable anti-tumor, anti-bacterial, anti-fungal, anti-inflammatory or immunosuppressive activities (Bull, A. T. et al. 2000 *Microbiol Mol Biol Rev* 64:573; Cragg, G. M. & D. J. Newman 2002 *Trends Pharmacol Sci* 23:404; Kerr, R. G. & S. S. Kerr 1999 *Exp Opin Ther Patents* 9:1207; Moore, B. S 1999 *Nat Prod Rep* 16:653; Faulkner, D. J. 2001 *Nat Prod Rep* 18:1; Mayer, A. M. & V. K. Lehmann 2001 *Anticancer Res* 21:2489), validating the utility of this source for isolating invaluable therapeutic agents. Further, the isolation of novel anti-cancer and anti-microbial agents that represent alternative mechanistic classes to those currently on the market will help to address resistance concerns, including any mechanism-based resistance that may have been engineered into pathogens for bioterrorism purposes.

SUMMARY OF THE INVENTION

Some embodiments include a lyophilized formulation comprising Salinosporamide A or an analog thereof. One embodiment includes a bulking agent. In one embodiment, the bulking agent comprises polyvinylpyrrolidone, a sugar, a sugar analog, or mixtures thereof. In one embodiment, the bulking agent comprises mannitol, lactose, trehalose, a cyclodextrin or mixtures thereof. In one embodiment, the bulking agent comprises sucrose. In one embodiment, the cyclodextrin is selected from the group consisting of a hydroxypropyl beta-cyclodextrin, a sulfobutylether beta-cyclodextrin, or mixtures thereof. In one embodiment, the bulking agent comprises KOLLIDON®. In one embodiment, the bulking agent comprises mannitol and sucrose.

Another embodiment includes a container comprising lyophilized Salinosporamide A or an analog thereof. In one embodiment, a bulking agent is included in the container. In one embodiment, the container comprises from about 0.2 to 4 mg of Salinosporamide A or an analog thereof. In one embodiment, the container is a type 1 flint tubing vial.

Another embodiment includes a method of lyophilizing compounds comprising β lactone rings, for example, Salinosporamide A or analog thereof, including dissolving the Salinosporamide A or analog thereof and a bulking agent in a solvent or co-solvent system, freezing the resulting solution, and drying the frozen solution. In one embodiment, the solvent comprises an alcohol. In one embodiment, the alcohol is t-butyl alcohol. In one embodiment, the co-solvent system comprises t-butyl alcohol and water. One embodiment includes dissolving the Salinosporamide A or analog thereof in an alcohol, dissolving the bulking agent in water, and mixing the resulting two solutions.

Another embodiment includes a method of administering Salinosporamide A or an analog thereof, including reconstituting the Salinosporamide A or analog thereof by adding a solvent or co-solvent diluent to a lyophilized formulation of the Salinosporamide A or analog thereof, and injecting the resulting solution into a patient. One embodiment includes storing the solution from about 2° C. to about 8° C. prior to injection.

Other embodiments include a method of treating cancer, inflammation, or an infectious disease, comprising administering to a patient or animal a formulation of Salinosporamide A or analog thereof prepared from a lyophilized product described above. In one embodiment, the cancer is selected from one or more of breast cancers; osteosarcomas, angiosarcomas, fibrosarcomas and other sarcomas; leukemias; sinus tumors; ovarian, uretal, bladder, prostate and other genitourinary cancers; colon, esophageal and stomach cancers and other gastrointestinal cancers; rectal cancers; lung cancers; lymphomas; myelomas; pancreatic cancers; liver cancers; kidney cancers; endocrine cancers; skin cancers; melanomas; angiomas; and brain or central nervous system (CNS; glioma) cancers. In one embodiment, the infectious disease is selected from one or more of infection with *B. anthracis, Plasmodium, Leishmania*, and *Trypanosoma*. In one embodiment, the administration comprises injecting the formulation into the patient. In one embodiment, the administration comprises administering the formulation intravenously.

DETAILED DESCRIPTION OF CERTAIN EMBODIMENTS

Figure 1:
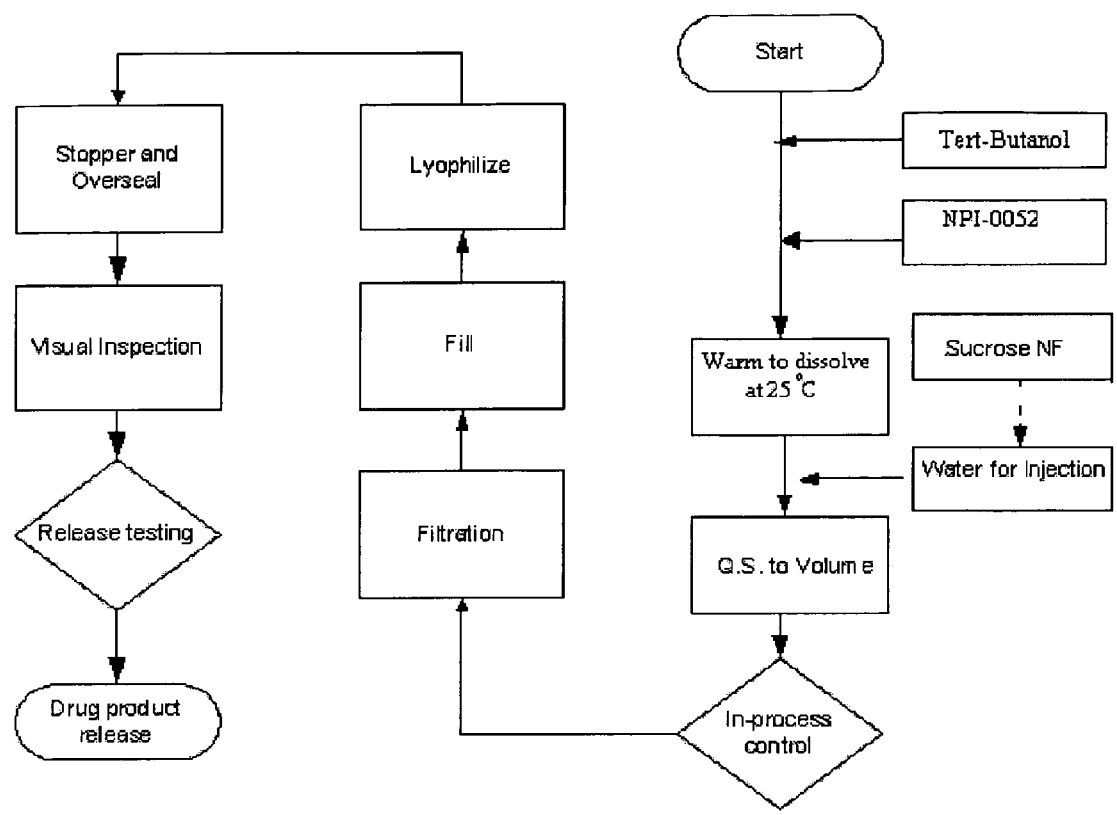
FIG. 1 is a flow chart illustrating methods of manufacturing lyophilized formulations.
Figure 2:
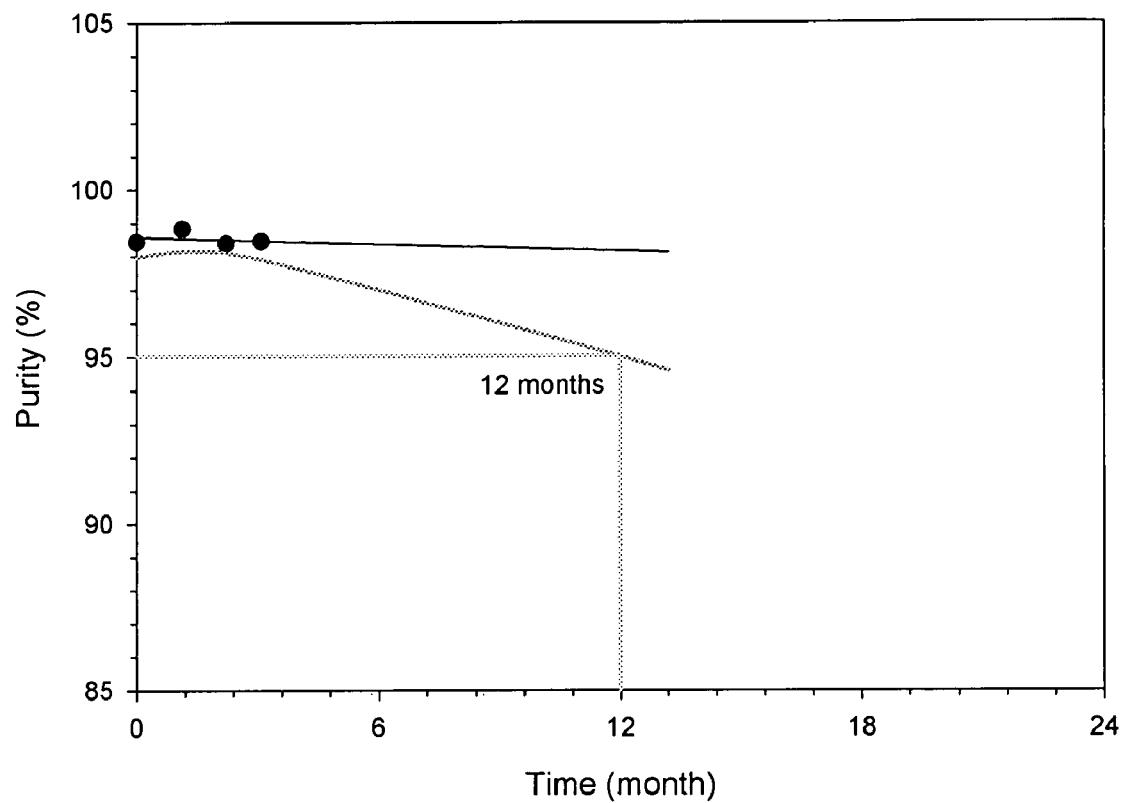
FIG. 2 is a graph showing results of a projected shelf life analysis using a 95% confidence interval for a lyophilized Salinosporamide A formulation (Lot# NPI-0052-06-107) stored at −20° C.
Figure 3:
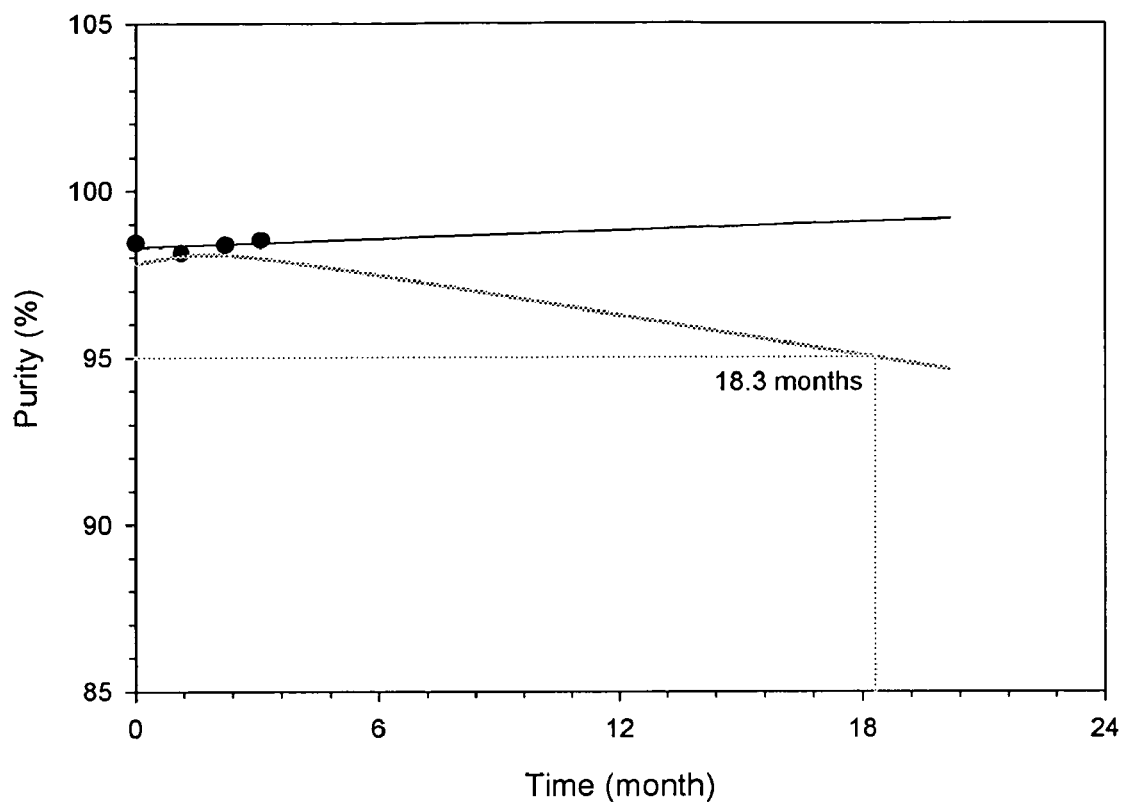
FIG. 3 is a graph showing results of a projected shelf life analysis using a 95% confidence interval for a lyophilized Salinosporamide A formulation (Lot# NPI-0052-06-107) stored at 5° C.

Salinosporamide A (NPI-0052) is a potent 20S proteasome inhibitor that is currently in clinical development for the treatment of cancer. The structure of Salinosporamide A is:

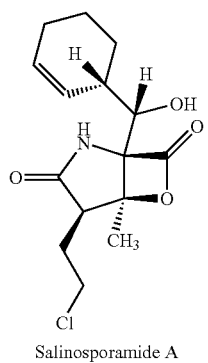

Salinosporamide A

Salinosporamide A and its analogs have various biological activities. For example, the compounds have chemosensitizing activity, anti-microbial, anti-inflammation, radiosensitizing, and anti-cancer activity. Studies have been conducted that show Salinospormide A and its analogs have proteasome inhibitory activity, effect NF-κB/IκB signaling pathway, and have anti-anthrax activity. Salinosporamide A and several analogs, as well as biological activity of the same, are described in U.S. Provisional Patent Applications Nos. 60/480,270, filed Jun. 20, 2003; 60/566,952, filed Apr. 30, 2004; 60/627,461, filed Nov. 12, 2004; 60/633,379, filed Dec. 3, 2004; 60/643,922, filed Jan. 13, 2005; 60/658,884, filed Mar. 4, 2005; 60/676,533, filed Apr. 29, 2005; 60/567,336, filed Apr. 30, 2004; 60/580,838, filed Jun. 18, 2004; 60/591,190, filed Jul. 26, 2004; 60/627,462, filed Nov. 12, 2004; 60/644,132, filed Jan. 13, 2005; 60/659,385, filed Mar. 4, 2005; 60/790,168, filed Apr. 6, 2006; 60/816,968, filed Jun. 27, 2006; 60/836,155, filed Aug. 7, 2006; 60/844,132, filed Sep. 12, 2006; 60/885,379, filed Jan. 17, 2007; 60/791,625, filed Apr. 13, 2006; 60/797,553, filed May 3, 2006 and 60/849,908, filed Oct. 5, 2006; U.S. patent application Ser. Nos. 10/871,368, filed Jun. 18, 2004; 11/118,260, filed Apr. 29, 2005; 11/412,476, filed Apr. 27, 2006; 11/453,374, filed Jun. 15, 2006; and 11/517,899, filed Sep. 8, 2006; and International Patent Applications Nos. PCT/US2004/019543, filed Jun. 18, 2004; PCT/US2005/044091, filed Dec. 2, 2005; PCT/US2005/014846, filed Apr. 29, 2005; and PCT/US2006/016104, filed Apr. 27, 2006; each of which is hereby incorporated by reference in its entirety.

In order to develop a suitable parenteral formulation and manufacturing process for Salinosporamide A and its analogs, factors such as the potency, solubility and chemical stability of the active pharmaceutical ingredient (API) were considered. The API is stable for at least 12 months when stored at −20° C. desiccated but is labile in aqueous solution at neutral and basic pH values. The predominant degradation pathway identified under these conditions involves hydrolysis of the β-lactone ring with subsequent elimination of chlorine.

Accordingly, in some embodiments, a dry powder formulation of Salinosporamide A is provided that may be stably stored for prolonged periods prior to use. The powder formulation may then be reconstituted using a suitable solvent or co-solvent system prior to injection into a patient (e.g., IV bolus injection or IV infusion). In some embodiments, the reconstituted formulation may be administered to animals, for example, mammals. In some embodiments, the dry powder formulation is a lyophilized formulation. In some embodiments, the lyophilized formulation includes the API and a bulking agent. Non-limiting examples of suitable bulking agents include polyvinylpyrrolidone (povidone), a sugar, a sugar analog, or mixtures thereof. Non-limiting examples of suitable sugars or sugar analogs include sucrose, mannitol, lactose, trehalose, and cyclodextrins. Non-limiting examples of suitable cyclodextrins include hydroxypropyl beta-cyclodextrin and sulfobutylether beta-cyclodextrin. In one embodiment, the bulking agent is KOLLIDON® 12 PF or 17 PF (BASF, Germany). In one embodiment, the bulking agent is mannitol. In another embodiment, the bulking agent is a combination of mannitol and sucrose. In yet another embodiment, the bulking agent is sucrose.

In some embodiments, the lyophilized formulations described above are placed in vials in which the formulation can be reconstituted with a suitable solvent or co-solvent. In various embodiments, each vial comprises from about 0.2 mg to about 4 mg, from about 1 mg to about 3 mg, from about 2 mg to about 4 mg, or from about 1.5 mg to about 2.5 mg of API. In one embodiment, each vial comprises about 2 mg of API. In various embodiments, each vial comprises from about 10 mg to about 100 mg, from about 20 mg to about 90 mg, from about 30 mg to about 80 mg, from about 40 mg to about 80 mg, or from about 60 mg to about 80 mg of bulking agent.

In some embodiments, a lyophilized formulation as described above may be stored at about 2° C. to about 8° C. or alternatively below −10° C. (e.g., about −20° C.) for prolonged periods without significant degradation. In various embodiments, the lyophilized formulation maintains purity in excess of about 95% after about 6 months, 12 months, or 18 months of storage. In vials containing about 2 mg of API and 80 mg bulking agent, the moisture content may be below about 2 mg, 1.5 mg, 1 mg, or 0.5 mg and the residual alcohol content may be below about 6 mg, 4 mg, or 2 mg. Such low solvent amounts may support the stability of the API during storage.

In some embodiments, the dry powder formulation described above is obtained by lyophilization of a bulk solution of the API and the bulking agent. In one embodiment, the solvent used in the pre-lyophilized solution is non-aqueous. In some embodiments, the non-aqueous solvent is an alcohol. In one embodiment, the alcohol is t-butyl alcohol. In some embodiments, the solvent is a co-solvent system. In some embodiments, the co-solvent system is a mixture of water with an alcohol. In one embodiment, the alcohol is t-butyl alcohol. In various embodiments, the co-solvent system comprises from about 5% to about 30%, from about 10% to about 25%, or from about 15% to about 20% water. In some embodiments, the pH of the solution is adjusted using a suitable acid, base, or buffer. In one embodiment, diluted HCl is used to adjust the pH. In some embodiments comprising a co-solvent mixture, the pH of water is adjusted prior to mixture. In various embodiments, the pH of the water is adjusted to be from about 3.0 to about 5.0.

Some embodiments include a method of manufacturing the lyophilized formulation described above. For example, FIG. 1 depicts a flow chart illustrating one suitable manufacturing process. Depending on the particular embodiment, steps may be added to those depicted in the flowchart or some steps may be removed. In addition, the order of steps may be rearranged depending on the application. In the process depicted in FIG. 1, t-butyl alcohol is added to an appropriate vessel followed by addition of the API (e.g., Salinosporamide A (NPI-0052)). The API is dissolved in the t-butyl alcohol by warming. In some embodiments, a shear mixer is used. Separately, the bulking agent (e.g., sucrose) is dissolved in water. The water solution is then added to the t-butyl alcohol solution. Additional t-butyl alcohol is added to obtain the desired final volume. In process control is then performed on the resulting solution. In process control may include HPLC assays to determine potency and purity of the API, checking the fill volume (e.g., 2.0 mL+/−0.05 mL), checking the specific gravity (e.g., 0.840+/−0.005), checking the bioburden (e.g., <10 cfu/100 ml), and checking the clarity of the solution.

If the solution passes the in-process control, it is then filtered such as by sterile filtration using a 2" OPTICAP® DURAPORE® PVDF 0.22 µm membrane (Millipore, Billerica, Mass.) (e.g., for a 12 L batch). Filling prior to lyophilization may be conducted at room temperature or from about 2° C. to about 8° C. The solution is then lyophilized. The lyophilization cycle may include annealing at about −15° C. (e.g., for about 1-4 hours), freezing at about −40° C. to about −50° C. (e.g., for from about 1 to about 4 hours), first drying at about −31° C. (e.g., for about 24 hours), second drying at about 25° C. (e.g., for about 30 hours), and unloading at about 5° C. or 20° C. The chamber vacuum used may be about 200 mTorr. The lyophilized product may then be stoppered and oversealed prior to visual inspection, release testing, and final product release. In some embodiments, packaging includes using a SCHOTT® Type 1 USP 20 mm flint tubing vial (Schott North America, Inc., Elmsford N.Y.) with a West FLUROTEC® coated stopper and a West flip-off seal (West Pharmaceutical Services, Lionville, Pa.).

The lyophilized API may be reconstituted into a solution using any suitable solvent or co-solvent system. Non-limiting solvent systems are described in more detail in U.S. Provisional Application No. 60/849,908, filed Oct. 5, 2006, which is incorporated herein by reference in its entirety. In one embodiment, the solvent system comprises a mixture of polyethylene glycol (for example, PEG-400, or PEG-300), ethanol, and a citrate buffer. In another embodiment, the solvent system comprises a mixture of propylene glycol, ethanol, and citrate buffer. In one embodiment, about 10 ml or about 20 ml of the solvent system may be added to a vial containing about 2 mg of API to produce a 0.2 or 0.1 mg/ml dosing solution, respectively. In some embodiments, a reconstituted solution of about 0.01 mg/ml, about 0.02, about 0.03 mg/ml, about 0.04 mg/ml, about 0.05 mg/ml, about 0.06 mg/ml, about 0.07 mg/ml, about 0.08 mg/ml, or about 0.09 mg/ml is prepared. The reconstituted solution may then be administered to a patient (e.g., via IV injection or infusion). In some embodiments, the reconstituted solution may be administered to an animal, for example, a mammal, for example, a rodent. In some embodiments, the dosing solution is refrigerated and administered within 3-5 hours to avoid hydrolytic degradation. In another embodiment, the refrigerated dosing solution is administered within 8-24 hours of reconstitution. In some embodiments, the dosing solution is administered at room temperature within 1-3 hours.

In various embodiments, the formulations, methods, uses, and kits described herein include any compound comprising a β lactone ring, for example, Salinosporamide A. Techniques are provided that allow for the compounding of bulk solutions and subsequent lyophilization of β lactone containing compounds while protecting against hydrolysis, which is an inherent problem with formulating such compounds.

EXAMPLES

Example 1

HPLC Protocols for Evaluating Purity and Potency of Lyophilized API

To evaluate the purity and potency of lyophilized Salinosporamide A, an HPLC protocol was developed allowing detection of Salinosporamide A and its degradants in the presence of the bulking agent(s). For each protocol, the lyophilized formulation was reconstituted in a diluent comprising 0.2% TFA in 45% water/55% acetonitrile. 4.0 mL of the diluent was added to vials containing lyophilized formulations comprising 2 mg of Salinosporamide A. The contents were mixed until all solids were dissolved and a clear solution obtained. After reconstitution, the theoretical concentration of Salinosporamide A is 0.5 mg/mL.

Protocol for Sucrose as the Bulking Agent

Five calibration solutions of Salinosporamide A were prepared having concentrations of 40 µg/mL, 200 µg/mL, 500 µg/mL, 600 µg/mL, and 800 µg/mL, respectively. As a check of system suitability, the 500 µg/mL standard solution is used as a check standard and is injected six times at the beginning of the sequence after the diluent injection, two injections after every ten sample injections, and two injections at the end of the run to ensure system suitability throughout the entire run. The % RSD of the area response for the six suitability injections at the beginning of the run plus the check standard injections is checked to be ≦2.0%. The chromatographic conditions were as indicated in Table 1.

TABLE 1

| Chromatographic conditions for sucrose containing samples. | | | |
|---|---|---|---|
| Column: | ACE C18, 150 × 4.6 mm, 5 µm, 100 Å | | |
| Flow rate: | 1.5 mL/min | | |
| Column temperature: | 30° C. | | |
| Autosampler temperature: | 5° C. | | |
| Inject volume: | 50 µL (with needle wash using ACN) | | |
| Run time: | 41 min. | | |
| Mobile Phase: | Eluant A: 0.01% TFA in pure water or HPLC water | | |
| | Eluant B: 0.01% TFA in HPLC acetonitrile (ACN) | | |
| Gradient Table: | Time (min) | Eluant A (%) | Eluant B (%) |
| | 0 | 95 | 5 |
| | 23 | 55 | 45 |
| | 32 | 20 | 80 |
| | 36 | 0 | 100 |
| | 37 | 95 | 5 |
| | 41 | 95 | 5 |
| | Signal: | | |
| DAD Detector Setting | Wavelength (nm) | Band Width | Reference |
| | 210 | 4 | Off |
| | 220 | 4 | Off |
| | 230 | 4 | Off |
| | 240 | 8 | Off |
| | 250 | 8 | Off |

Spectrum: Store all data in the range of 200-600 nm with step size of 2.0 nm.
Time: Stop time as pump.
Required lamp: UV and Vis.
Autobalance: Prerun.
Slit: 4 nm.
Margin for Negative absorbance: 100 mAU The typical injection sequence was: diluent (2 injections) → 500 µg/mL standard (6 injections) → 40 µg/mL standard → 200 µg/mL standard → 500 µg/mL standard → 600 µg/mL standard → 800 µg/mL standard → 500 µg/mL standard (2 injections) → working sample 1 (2 injections) → working sample 2 (2 injections) → working sample 3 (2 injections) → etc. → 500 µg/mL standard (2 injections) → diluent.

The peak areas from the single injections of the calibration solutions were plotted versus the concentration to determine a linear regression line. The concentration of Salinosporamide A from the test samples are determined based on this calibration curve. Potency is determined as the percent of the measured concentration relative to the theoretical concentration. Peak areas for certain impurities are corrected by multiplication by correction factors based on the Relative Response Factor (RRF). The correction factors listed in Table 2 were used for Salinosporamide A (NPI-0052) and several impurities.

TABLE 2

HPLC correction factors.

| | 220 nm | | | 240 nm | | |
|---|---|---|---|---|---|---|
| Peak ID | RF | RRF | Correction Factor | RF | RRF | Correction Factor |
| NPI-0052 | 8.557 | 1.000 | 1.000 | 3.183 | 1.000 | 1.000 |
| NPI-0049 | 80.699 | 9.431 | 0.106 | 21.844 | 6.862 | 0.146 |
| NPI-2083 | 80.699 | 9.431 | 0.106 | 21.844 | 6.862 | 0.146 |
| NPI-0050 | 12.130 | 1.418 | 0.705 | 27.143 | 8.527 | 0.117 |
| NPI-2107 | 181.430 | 21.202 | 0.0472 | 61.311 | 19.261 | 0.0519 |

The relative retention time, molecular weight, and m/z data were determined for Salinosporamide A (NPI-0052) and related compounds based on a chromatogram run on an MSD system using UV detection at 220 nm. The results are indicated in Table 3.

TABLE 3

Chromatograph and mass spectrometry data for Salinosporamide A (NPI-0052) and related compounds.

| Compound ID | Mol. Weight | Retention Time (min.) | Relative Retention Time (RRT) | m/z [M + H]+ |
|---|---|---|---|---|
| NPI-2055 | 295.3 | 8.512 | 0.398 | 296.1 |
| NPI-2107 | 173.6 | 12.717 | 0.594 | 174.1 |
| NPI-2054 | 331.8 | 13.247 | 0.617 | 332.1 |
| NPI-2063 | 265.3 | 16.008 | 0.753 | 266.1 |
| NPI-2082 | 233.3 | 17.666 | 0.825 | 234.2 |
| NPI-0049/2083 | 269.8 | 18.530 | 0.866 | 270.0 |
| NPI-0047 | 279.3 | 19.049 | 0.890 | 280.1 |
| NPI-2065 | 313.8 | 20.734 | 0.969 | 314.1 |
| NPI-0052 | 313.8 | 21.402 | 1.000 | 314.1 |
| NPI-2080 | 293.4 | 22.066 | 1.031 | 294.1 |
| NPI-0050 | 251.8 | 27.583 | 1.289 | 252.1 |
| Following data are from individual injections of NPI-0049 and NPI-2083 | | | | |
| NPI-0049 | 269.8 | 18.517 | 0.865 | 270.0 |
| NPI-2083 | 269.8 | 18.453 | 0.862 | 270.0 |

The chemical structures of the above-identified compounds are:

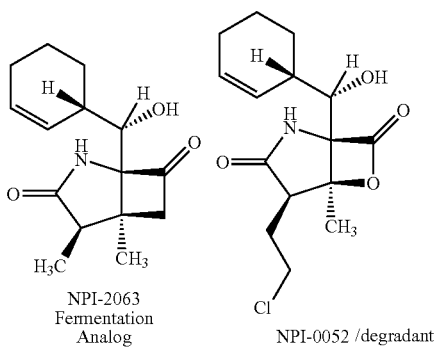

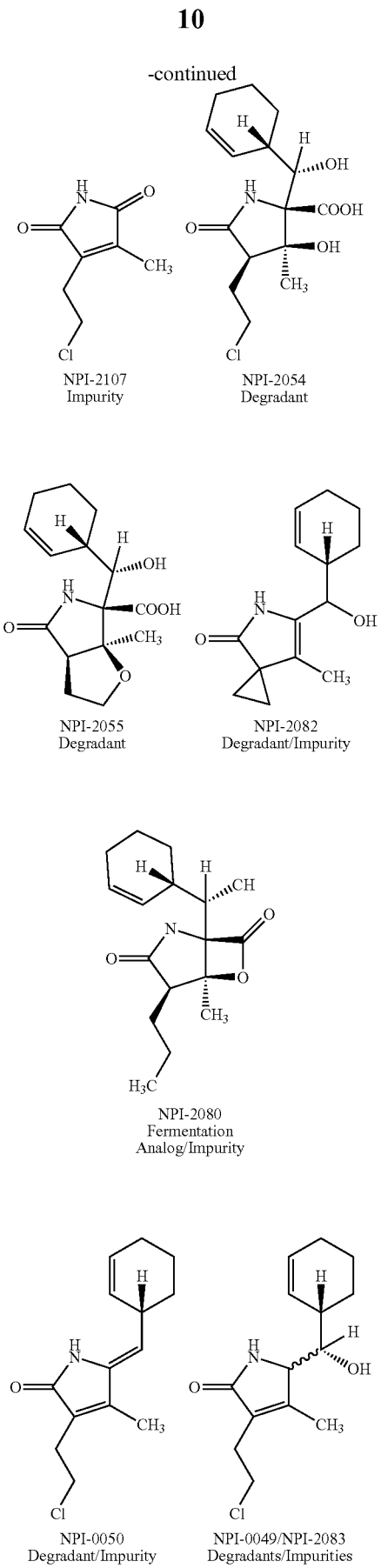

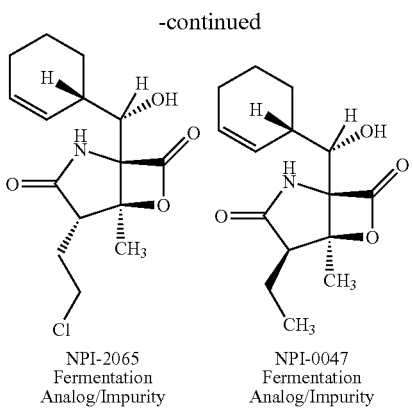

NPI-2065
Fermentation
Analog/Impurity

NPI-0047
Fermentation
Analog/Impurity

Protocol for Povidone as the Bulking Agent

Povidone interferes with HPLC analysis of Salinosporamide A and its degradants when UV detection is used, especially at low wavelength. Povidone is a polymeric compound that generally elutes as a broad peak on reverse phase columns, which makes it challenging to separate from analyte peaks. Accordingly, a reverse phase HPLC gradient method that separates povidone from Salinosporamide A and its degradants was developed. Both evaporative light scattering (ELS) and UV detection were evaluated to optimize quantitation and good chromatographic results. Degradants and impurities were identified using mass spectroscopy. This method was tested for linearity, accuracy, precision, specificity, robustness and quantitation and detection limits. A comparative study using the ELS and UV detection techniques were performed.

Seven calibration solutions of Salinosporamide A were prepared having concentrations of 50 µg/mL, 100 µg/mL, 240 µg/mL, 500 µg/mL, 600 µg/mL, 720 µg/mL, and 800 µg/mL, respectively. As a check of system suitability, the 500 µg/mL standard solution is used as a check standard and is injected six times at the beginning of the sequence after the diluent injection, two injections after every ten sample injections, and two injections at the end of the run to ensure system suitability throughout the entire run. The % RSD of the area response for the six suitability injections at the beginning of the run plus the check standard injections is checked to be ≦2.0%. The chromatographic conditions were as indicated in Table 4.

TABLE 4

Chromatographic conditions for povidone containing samples.

| Column: | Phenomenex Synergi POLAR-RP C18, 4µ, 250 × 4.6 mm 80 Å |
| --- | --- |
| Flow rate: | 1.0 mL/min |
| Column temperature: | 40° C. |
| Autosampler temperature: | 4° C. |
| Inject volume: | 50 µL (with needle wash using ACN) |
| Run time: | 56 min. |
| Mobile Phase: | Eluant A: 0.01% TFA in pure water or HPLC water<br>Eluant B: 0.01% TFA in HPLC grade tetrahydrofurn (THF) containing 5% HPLC grade acetonitrile (ACN) |
| Gradient Table: | Time (min) | Eluant A (%) | Eluant B (%) |

| Time (min) | Eluant A (%) | Eluant B (%) |
| --- | --- | --- |
| 0 | 100 | 0 |
| 10 | 95 | 5 |
| 12 | 90 | 10 |
| 15 | 90 | 10 |

TABLE 4-continued

Chromatographic conditions for povidone containing samples.

| 17 | 80 | 20 |
| --- | --- | --- |
| 30 | 50 | 50 |
| 40 | 50 | 50 |
| 42 | 35 | 65 |
| 46 | 10 | 90 |
| 48 | 10 | 90 |
| 50 | 80 | 20 |
| 52 | 95 | 5 |
| 54 | 100 | 0 |
| 56 | 100 | 0 |

Signal:

| DAD Detector Setting | Wavelength (nm) | Band Width | Reference |
| --- | --- | --- | --- |
| | 210 | 4 | Off |
| | 220 | 4 | Off |
| | 230 | 4 | Off |
| | 240 | 8 | Off |
| | 250 | 8 | Off |

ELSD Setting

| Nitrogen Gas Pressure | 4.0 Bar |
| --- | --- |
| Gain | 7 |
| Nebulization Temperature | 40° C. |

Spectrum: Store all data in the range of 200-600 nm with step size of 2.0 nm.
Time: Stop time as pump.
Required lamp: UV and Vis.
Autobalance: Prerun.
Slit: 4 nm.
Margin for Negative absorbance: 100 mAU The typical injection sequence was: diluent (2 injections) → 500 µg/mL standard → (6 injections) → 50 µg/mL standard → 100 µg/mL standard → 240 µg/mL standard → 500 µg/mL standard → 600 µg/mL standard → 720 µg/mL standard → 800 µg/mL standard → 500 µg/mL standard (2 injections → working sample 1 (2 injections → working sample 2 (2 injections → working sample 3 (2 injections → etc. → 500 µg/mL standard (2 injections → diluent.

The peak areas from the single injections of the calibration solutions were plotted versus the concentration to determine a linear regression line. The concentration of Salinosporamide A from the test samples are determined based on this calibration curve. Potency is determined as the percent of the measured concentration relative to the theoretical concentration. Peak areas for certain impurities are corrected by multiplication of correction factors based on the Relative Response Factor (RRF). The correction factors listed in Table 5 were used.

TABLE 5

HPLC correction factors.

| | 240 nm | | |
| --- | --- | --- | --- |
| Peak ID | RF | RRF | Correction Factor |
| NPI-0052 | 5.501 | 1.000 | 1.000 |
| NPI-0050 | 39.898 | 7.252 | 0.138 |
| NPI-0049 | 23.407 | 4.255 | 0.235 |

The relative retention time, molecular weight, and m/z data were determined for Salinosporamide A (NPI-0052) and related compounds based on a chromatogram run on an MSD system using UV detection at 240 nm. The results are indicated in Table 6.

TABLE 6

Chromatograph and mass spectrometry data for Salinosporamide A (NPI-0052) and related compounds.

| Compound ID | Mol. Weight | Retention Time (min.) | Relative Retention Time (RRT) | m/z [M + H]+ |
|---|---|---|---|---|
| NPI-2055 | 295.3 | 21.880 | 0.629 | 296.1 |
| NPI-2107 | 173.6 | N/D | N/D | 174.1 |
| NPI-2054 | 331.8 | N/D | N/D | 332.1 |
| NPI-2082 | 233.3 | 28.219 | 0.812 | 234.2 |
| NPI-2083 | 269.8 | 29.280 | 0.842 | 270.0 |
| NPI-0049 | 269.8 | 29.717 | 0.855 | 270.0 |
| NPI-2063 | 265.3 | 29.929 | 0.861 | 266.1 |
| NPI-0047 | 279.3 | 32.059 | 0.922 | 280.1 |
| NPI-2080 | 293.4 | 33.809 | 0.973 | 294.1 |
| NPI-2065 | 313.8 | 34.761 | 1.00 | 314.1 |
| NPI-0052 | 313.8 | 34.761 | 1.00 | 314.1 |
| NPI-0050 | 251.8 | 35.493 | 1.02 | 252.1 |

N/D: Not determined

Example 2

Non-Aqueous Lyophilizing Solution 2.0 mg Salinosporamide A was added to a 20 ml Type 1 USP flint tubing vial and t-butyl alcohol was added to bring the total volume to 1 ml. A clear solution was obtained. The t-butyl alcohol was essentially removed during lyophilization to produce a lyophilized formulation.

Example 3

Water/T-Butyl Alcohol Lyophilizing Solution (Kollidon 12 PF)

2.0 mg Salinosporamide A, 30.0 mg of KOLLIDON® (12 PF), and t-butyl alcohol were added to a 20 ml Type 1 USP flint tubing vial. 100 mg of water (water pH was adjusted to pH 3.0-5.0 with diluted HCl) and additional t-butyl alcohol were added to bring the total volume to 2 ml. A clear solution was obtained. The t-butyl alcohol and water were essentially removed during lyophilization to produce a lyophilized formulation.

Example 4

Water/T-Butyl Alcohol Lyophilizing Solution (Kollidon 17 PF)

2.0 mg Salinosporamide A, 30.0 mg of KOLLIDON® (17 PF), and t-butyl alcohol were added to a 20 ml Type 1 USP flint tubing vial. 100 mg of water (water pH was adjusted to pH 3.0-5.0 with diluted HCl) and additional t-butyl alcohol were added to bring the total volume to 2 ml. A clear solution was obtained. The t-butyl alcohol and water were essentially removed during lyophilization to produce a lyophilized formulation.

Example 5

Water/T-Butyl Alcohol Lyophilizing Solution (Mannitol)

2.0 mg Salinosporamide A and t-butyl alcohol were added to a 20 ml Type 1 USP flint tubing vial. 20.0 mg of mannitol was dissolved in 380 mg of water (water pH was adjusted to pH 3.0-5.0 with diluted HCl) and added to the vial. Additional t-butyl alcohol was added to bring the total volume to 2 ml. A clear solution was obtained. The t-butyl alcohol and water were essentially removed during lyophilization to produce a lyophilized formulation.

Example 6

Water/T-Butyl Alcohol Lyophilizing Solution (Mannitol/Sucrose)

2.0 mg Salinosporamide A and t-butyl alcohol were added to a 20 ml Type 1 USP flint tubing vial. 60.0 mg of sucrose and 20 mg of mannitol were dissolved in 320 mg of water (water pH was adjusted to pH 3.0-5.0 with diluted HCl) and added to the vial. Additional t-butyl alcohol was added to bring the total volume to 2 ml. A clear solution was obtained. The t-butyl alcohol and water were essentially removed during lyophilization to produce a lyophilized formulation.

Example 7

Water/T-Butyl Alcohol Lyophilizing Solution (Sucrose)

2.0 mg Salinosporamide A and t-butyl alcohol were added to a 20 ml Type 1 USP flint tubing vial. 60.0 mg of sucrose was dissolved in 240 mg of water (water pH was adjusted to pH 3.0-5.0 with diluted HCl) and added to the vial. Additional t-butyl alcohol was added to bring the total volume to 2 ml. A clear solution was obtained. After lyophilization, the water and t-butyl alcohol content were measured. Water content was determined using the Karl Fischer coulometric method and t-butyl alcohol content was determined using a GC headspace method. The water content was 0.24 mg. The t-butyl alcohol content was 1.28 mg.

Example 8

Water/T-Butyl Alcohol Lyophilizing Solution (Sucrose)

2.0 mg Salinosporamide A and t-butyl alcohol were added to a 20 ml Type 1 USP flint tubing vial. 70.0 mg of sucrose was dissolved in 280 mg of water (water pH was adjusted to pH 3.0-5.0 with diluted HCl) and added to the vial. Additional t-butyl alcohol was added to bring the total volume to 2 ml. A clear solution was obtained. After lyophilization, the water and t-butyl alcohol content were measured. Water content was determined using the Karl Fischer coulometric method and t-butyl alcohol content was determined using a GC headspace method. The water content was 0.15 mg. The t-butyl alcohol content was 1.72 mg.

Example 9

Water/T-Butyl Alcohol Lyophilizing Solution (Sucrose)

2.0 mg Salinosporamide A and t-butyl alcohol were added to a 20 ml Type 1 USP flint tubing vial. 80.0 mg of sucrose was dissolved in 320 mg of water (water pH was adjusted to pH 3.0-5.0 with diluted HCl) and added to the vial. Additional t-butyl alcohol was added to bring the total volume to 2 ml. A clear solution was obtained. After lyophilization, the water and t-butyl alcohol content were measured. Water content was determined using the Karl Fischer coulometric method and t-butyl alcohol content was determined using a GC headspace method. The water content was 0.05 mg. The t-butyl alcohol content was 2.01 mg.

Example 10

Water/T-Butyl Alcohol Lyophilizing Solution (Sucrose)

2.0 mg Salinosporamide A and t-butyl alcohol were added to a 20 ml Type 1 USP flint tubing vial. 80.0 mg of sucrose was dissolved in 320 mg of water (water pH was adjusted to pH 3.0-5.0 with diluted HCl) and added to the vial. Additional t-butyl alcohol was added to bring the total volume to 2 ml. A clear solution was obtained. After lyophilization, the water and t-butyl alcohol content were measured. Water content was determined using the Karl Fischer coulometric method and t-butyl alcohol content was determined using a GC headspace method. The water content was 0.21 mg. The t-butyl alcohol content was 1.83 mg.

Example 11

Stability Studies

The potency and purity of the lyophilized formulations of Examples 7-10 were studied using the procedures described in Example 1 under various storage conditions and times. The measured potency for the various examples and conditions are indicated in Table 7 and the purity values are given in Table 8.

TABLE 7

Potency of lyophilized formulations.

| | 2 mg Salinosporamide A/ 80 mg Sucrose | | | | | 2 mg Salinosporamide A/ 60 mg Sucrose | |
|---|---|---|---|---|---|---|---|
| Elapsed Time (days) | Ex 9 −20° C. (%) | Ex 9 2-8° C. (%) | Ex 9 25° C. (%) | Ex 10 40° C. (%) | Ex 10 50° C. (%) | Ex 7 40° C. (%) | Ex 7 50° C. (%) |
| 0 | 94.9 | 94.9 | 94.9 | 97.4 | 97.4 | 95.5 | 95.5 |
| 7 | N/D | N/D | N/D | 100.9 | 98.8 | 98.8 | 98.8 |
| 15 | N/D | N/D | N/D | 94.9 | 96.7 | 99.3 | 99.9 |
| 28 | N/D | N/D | N/D | 94.7 | 89.7 | 95.3 | 94.5 |
| 35 | 94.7 | 88.7 | 90.7 | 93.3 | 87.6 | 94.2 | 92.0 |
| 56 | N/D | N/D | N/D | 95.5 | N/D | 98.4 | N/D |
| 69 | 94.3 | 94.9 | 94.8 | N/D | N/D | N/D | N/D |
| 96 | 98.2 | 100.1 | 95.9 | N/D | N/D | N/D | N/D |

N/D: Not determined

TABLE 8

Purity of lyophilized formulations.

| | 2 mg Salinosporamide A/ 80 mg Sucrose | | | | | 2 mg Salinosporamide A/ 60 mg Sucrose | |
|---|---|---|---|---|---|---|---|
| Elapsed Time (days) | Ex 9 −20° C. (%) | Ex 9 2-8° C. (%) | Ex 9 25° C. (%) | Ex 10 40° C. (%) | Ex 10 50° C. (%) | Ex 7 40° C. (%) | Ex 7 50° C. (%) |
| 0 | 98.4 | 98.4 | 98.4 | 98.7 | 98.7 | 98.7 | 98.7 |
| 7 | N/D | N/D | N/D | 98.1 | 93.4 | 98.4 | 94.7 |
| 15 | N/D | N/D | N/D | 97.6 | 92.8 | 98.2 | 94.1 |
| 28 | N/D | N/D | N/D | 97.4 | 91.1 | 98.0 | 93.6 |
| 35 | 98.8 | 98.1 | 98.4 | 97.6 | 94.7 | 97.6 | 92.7 |
| 56 | N/D | N/D | N/D | 96.6 | N/D | 97.4 | N/D |
| 69 | 98.4 | 98.4 | 97.6 | N/D | N/D | N/D | N/D |
| 96 | 98.5 | 98.5 | 97.7 | N/D | N/D | N/D | N/D |

N/D: Not determined

Figure 4:
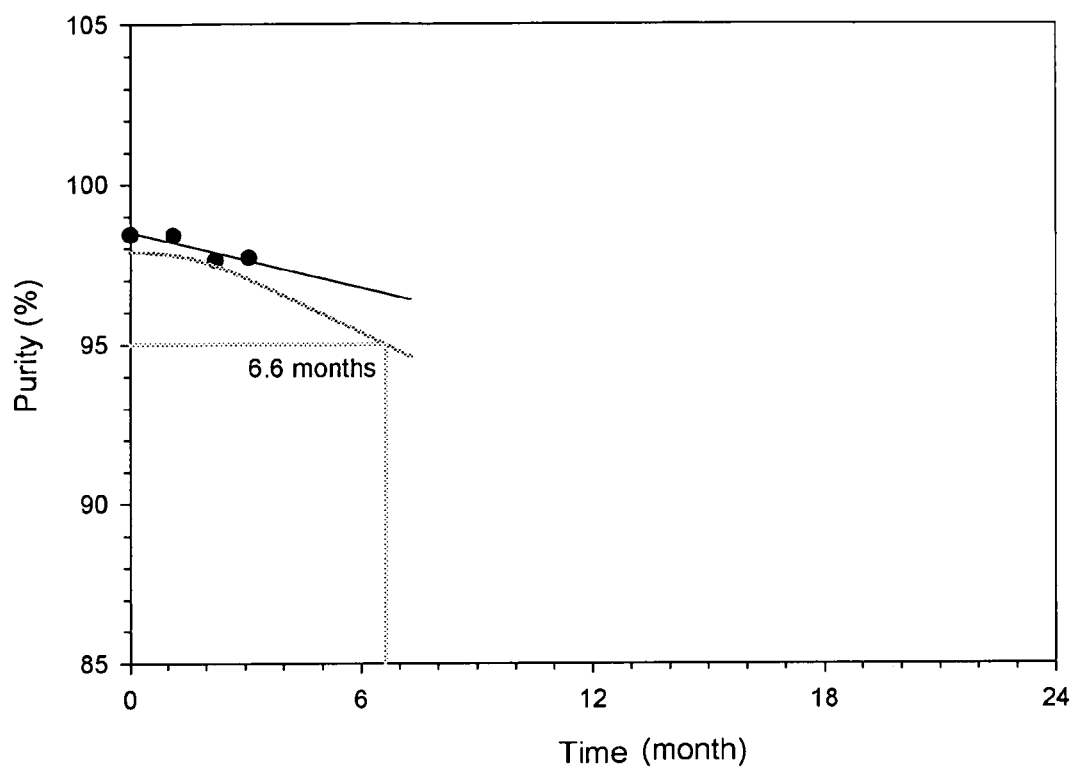
FIG. 4 is a graph showing results of a projected shelf life analysis using a 95% confidence interval for a lyophilized Salinosporamide A formulation (Lot# NPI-0052-06-107) stored at 25° C.
Figure 5:
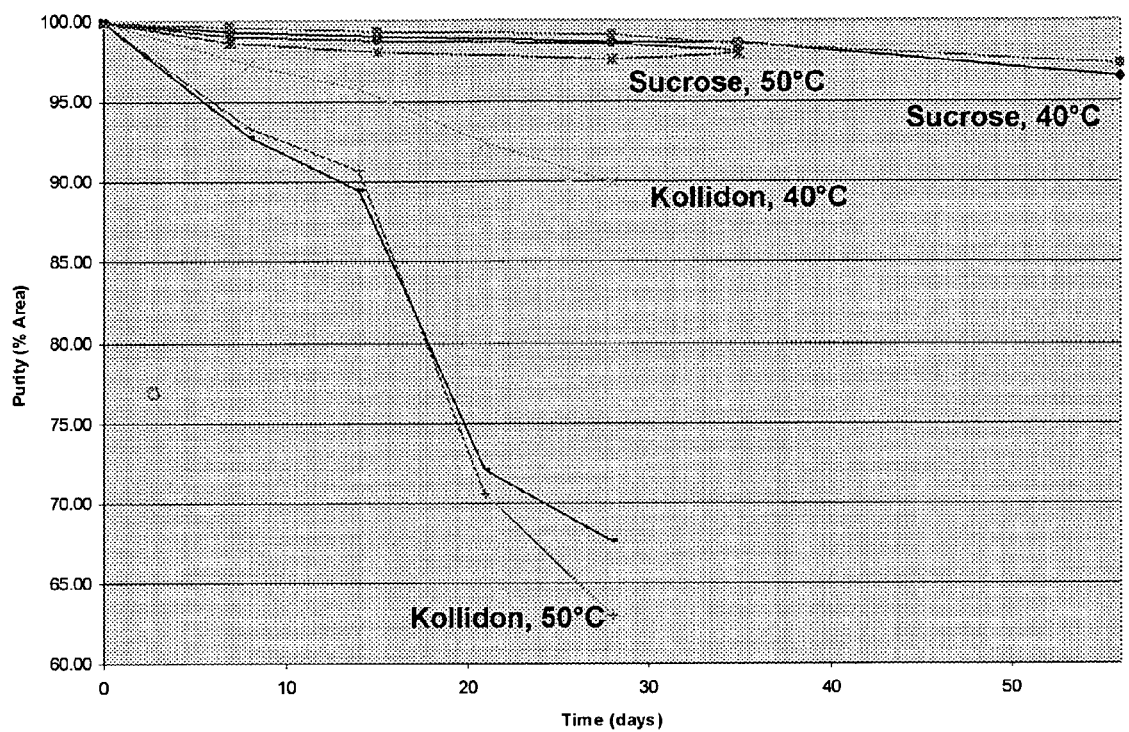
FIG. 5 is a graph showing an accelerated stability study for several lyophilized Salinosporamide A formulations stored at various temperatures, where Salinosporamide A purity was measured as a function of time. Two samples containing sucrose were prepared according to the methods of Examples 7 and 10, with 60 mg and 80 mg of sucrose, respectively. Two samples containing Kollidon were prepared according to the method of Examples 3 and 4 with the samples comprising KOLLIDON® 12 PF or KOLLIDON® 17 PF. At various times, the lyophilized product was reconstituted and the purity determined.
Figure 6:
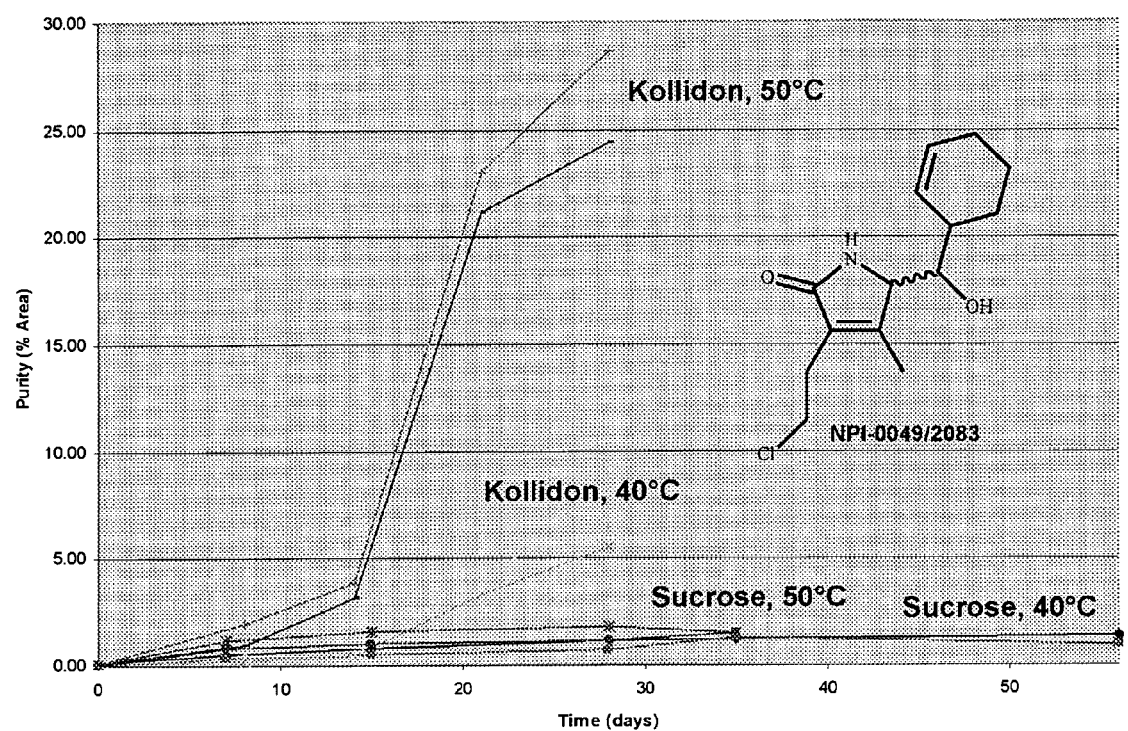
FIG. 6 is a graph showing an accelerated stability study for several lyophilized Salinosporamide A formulations stored at various temperatures, where the amount of the NPI-0049/2083 impurities was measured as a function of time. Two samples containing sucrose were prepared according to the methods of Examples 7 and 10, with 60 mg and 80 mg of sucrose, respectively. Two samples containing Kollidon were prepared according to the method of Examples 3 and 4 with the samples comprising KOLLIDON® 12 PF or KOLLIDON® 17 PF. At various times, the lyophilized product was reconstituted and the purity determined.

Based on the measured purity values of the Example 9 lyophilized product, a projected shelf life analysis was conducted using a 95% confidence interval. For various storage conditions, the amount time before purity dropped to 95% was projected. The results are depicted in FIGS. 4-6.

Figure 7:
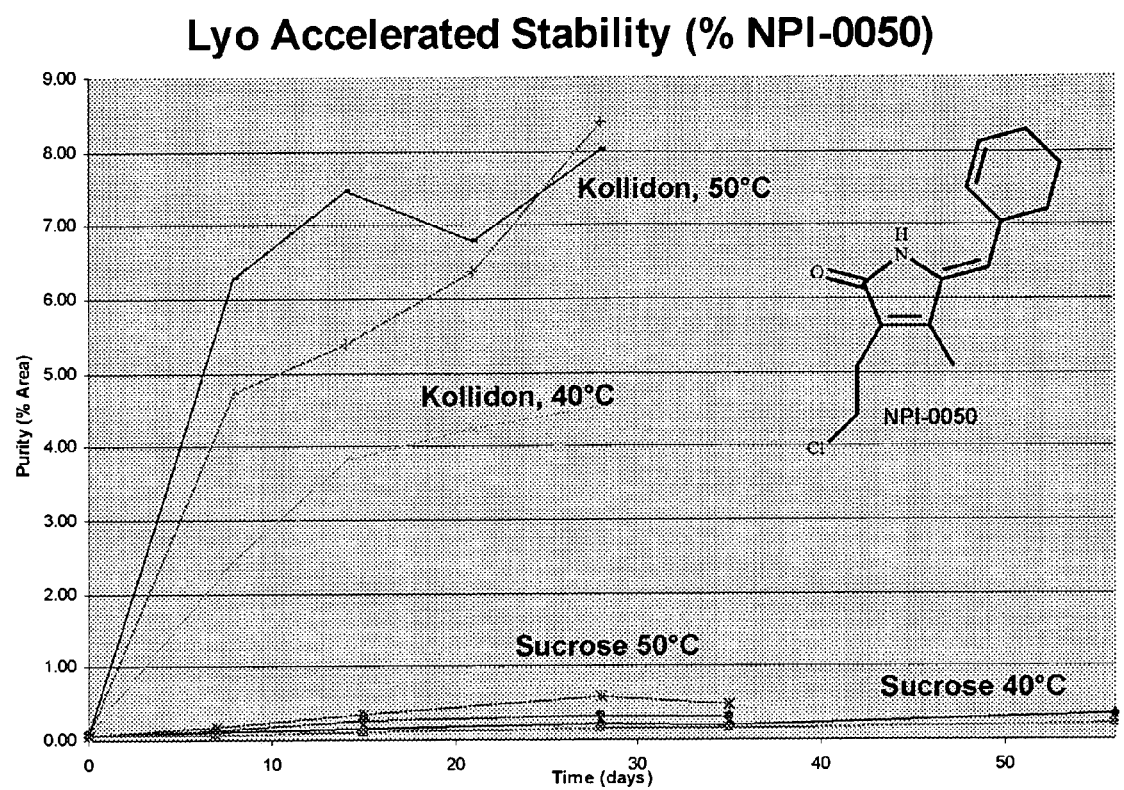
FIG. 7 is a graph showing an accelerated stability study for several lyophilized Salinosporamide A formulations stored at various temperatures, where the amount of the NPI-0050 impurity measured as a function of time. Two samples containing sucrose were prepared according to the methods of Examples 7 and 10, with 60 mg and 80 mg of sucrose, respectively. Two samples containing Kollidon were prepared according to the method of Examples 3 and 4 with the samples comprising KOLLIDON® 12 PF or KOLLIDON® 17 PF. At various times, the lyophilized product was reconstituted and the purity determined.

Accelerated stability studies were conducted on the lyophilized product of Examples 4, 7, and 10. The product was stored at various temperatures. At various times, the lyophilized product was reconstituted and the purity determined as discussed above. FIG. 5 depicts the resulting Salinosporamide A purity measured as a function of time. The two samples containing sucrose were from Examples 7 and 10 (60 mg and 80 mg of sucrose, respectively). The two samples containing Kollidon were prepared as in Example 4 with one being KOLLIDON® 12 PF and the other being KOLLIDON® 17 PF. FIG. 6 depicts the amount of the NPI-0049/2083 impurities measured as a function of time. FIG. 7 depicts the amount of the NPI-0050 impurity measured as a function of time. Among these samples, lyophilized product containing sucrose as the bulking agent exhibited the highest stability.

Example 12

Reconstitution Strategies

Various lyophilized compositions were reconstituted using various amounts of either propylene glycol (PG) or polyethylene glycol (PEG) with ethanol and citrate buffer (CB). The time required to successfully solubilize the lyophilate was measured. Tables 9-13 list the results using PG with 60 mg, 70 mg, 80 mg, 80 mg, and 40 mg sucrose in the lyophilate, respectively. Tables 14-17 list the results using PEG-400 with 60 mg, 70 mg, 80 mg, and 40 mg sucrose in the lyophilate, respectively.

TABLE 9

Reconstitution of Salinosporamide A/60 mg sucrose lyophilate using PG/EtOH/CB diluent.

| Diluent Composition | | | | |
|---|---|---|---|---|
| PG (%, v/v) | EtOH (%, v/v) | CB (%, v/v) | Diluent Volume (mL) | Dissolution Time |
| 40 | 10 | 50 | 20 | 5 min |
| 60 | 10 | 30 | 10 | >5 min |
| 50 | 0 | 50 | 10 | >5 min |
| 50 | 10 | 40 | 10 | 2 min |
| 50 | 20 | 30 | 10 | <2 min |
| 40 | 10 | 50 | 10 | >5 min |
| 40 | 20 | 40 | 10 | <2 min |
| 30 | 20 | 50 | 10 | >5 min |

TABLE 10

Reconstitution of Salinosporamide A/70 mg sucrose lyophilate using PG/EtOH/CB diluent.

| Diluent Composition | | | | |
|---|---|---|---|---|
| PG (%, v/v) | EtOH (%, v/v) | CB (%, v/v) | Diluent Volume (mL) | Dissolution Time |
| 40 | 10 | 50 | 20 | <5 min |
| 60 | 10 | 30 | 10 | 4.5 min |
| 50 | 10 | 40 | 10 | 4 min |
| 50 | 20 | 30 | 10 | <2 min |
| 40 | 20 | 40 | 10 | <2 min |

TABLE 11

Reconstitution of Salinosporamide A/80 mg sucrose lyophilate using PG/EtOH/CB diluent.

| Diluent Composition | | | | |
|---|---|---|---|---|
| PG (%, v/v) | EtOH (%, v/v) | CB (%, v/v) | Diluent Volume (mL) | Dissolution Time |
| 40 | 10 | 50 | 20 | 5 min |
| 60 | 10 | 30 | 10 | 2-5 min |
| 50 | 0 | 50 | 10 | >5 min |
| 50 | 10 | 40 | 10 | 2 min |
| 50 | 20 | 30 | 10 | 2 min |
| 40 | 10 | 50 | 10 | >5 min |
| 40 | 20 | 40 | 10 | 2 min |
| 30 | 20 | 50 | 10 | 2 min |

TABLE 12

Reconstitution of Salinosporamide A/80 mg sucrose lyophilate using PG/EtOH/CB diluent.

| Diluent Composition | | | | |
|---|---|---|---|---|
| PG (%, v/v) | EtOH (%, v/v) | CB (%, v/v) | Diluent Volume (mL) | Dissolution Time |
| 40 | 10 | 50 | 20 | 5 min |
| 40 | 10 | 50 | 10 | >5 min |
| 40 | 20 | 40 | 10 | 1 min |

TABLE 13

Reconstitution of Salinosporamide A/40 mg sucrose lyophilate using PG/EtOH/CB diluent.

| Diluent Composition | | | | |
|---|---|---|---|---|
| PG (%, v/v) | EtOH (%, v/v) | CB (%, v/v) | Diluent Volume (mL) | Dissolution Time |
| 40 | 10 | 50 | 20 | >5 min |
| 60 | 10 | 30 | 10 | >5 min |
| 50 | 0 | 50 | 10 | >5 min |
| 50 | 10 | 40 | 10 | >5 min |
| 50 | 20 | 30 | 10 | >5 min |
| 40 | 10 | 50 | 10 | >5 min |
| 40 | 20 | 40 | 10 | >5 min |
| 30 | 20 | 50 | 10 | >5 min |

TABLE 14

Reconstitution of Salinosporamide A/60 mg sucrose lyophilate using PEG/EtOH/CB diluent.

| Diluent Composition | | | | |
|---|---|---|---|---|
| PEG400 (%, v/v) | EtOH (%, v/v) | CB (%, v/v) | Diluent Volume (mL) | Dissolution Time |
| 50 | 20 | 30 | 10 | <2 min |
| 40 | 20 | 40 | 10 | <2 min |

TABLE 15

Reconstitution of Salinosporamide A/70 mg sucrose lyophilate using PEG/EtOH/CB diluent.

| Diluent Composition | | | | |
|---|---|---|---|---|
| PEG400 (%, v/v) | EtOH (%, v/v) | CB (%, v/v) | Diluent Volume (mL) | Dissolution Time |
| 50 | 10 | 40 | 10 | <5 min |
| 50 | 20 | 30 | 10 | <2 min |
| 40 | 20 | 40 | 10 | <2 min |

TABLE 16

Reconstitution of Salinosporamide A/80 mg sucrose lyophilate using PEG/EtOH/CB diluent.

| Diluent Composition | | | | |
|---|---|---|---|---|
| PEG400 (%, v/v) | EtOH (%, v/v) | CB (%, v/v) | Diluent Volume (mL) | Dissolution Time |
| 50 | 20 | 30 | 10 | <2 min |
| 40 | 20 | 40 | 10 | <2 min |

TABLE 17

Reconstitution of Salinosporamide A/40 mg sucrose lyophilate using PEG/EtOH/CB diluent.

| Diluent Composition | | | | |
|---|---|---|---|---|
| PEG400 (%, v/v) | EtOH (%, v/v) | CB (%, v/v) | Diluent Volume (mL) | Dissolution Time |
| 50 | 20 | 30 | 10 | >5 min |
| 40 | 20 | 40 | 10 | >5 min |

Example 13

Stability of Reconstituted Solution

The potency and purity of reconstituted lyophilate was determined using various diluents. The lyophilate included 70 mg of sucrose. Four different diluents were tested. Diluent I included 40% propylene glycol, 20% ethanol, and 40% citrate buffer (10 mM, pH 5.0). Diluent II included 50% propylene glycol, 20% ethanol, and 30% citrate buffer (10 mM, pH 5.0). Diluent III included 40% polyethylene glycol 400, 20% ethanol, and 40% citrate buffer (10 mM, pH 5.0). Diluent IV included 50% polyethylene glycol 400, 20% ethanol, and 30% citrate buffer (10 mM, pH 5.0). Table 18 lists the results as a function of time after reconstitution when the solution is stored at 5° C. Table 19 lists the results when the solution is stored at 25° C.

TABLE 18

Potency and purity of a Salinosporamide A stored at 5° C. after reconstitution from a Salinosporamide A/sucrose lyophilate.

| Time (h) | Potency (%) | Recovery Based on time t = 0 | Degradation rate (%/h) | Purity (%) |
|---|---|---|---|---|
| Diluent I | | | | |
| 0 | 100.80 | 100 | — | 98.25 |
| 3 | 100.37 | 99.57 | 0.14 | 98.05 |
| 5 | 100.06 | 99.26 | 0.15 | 98.09 |
| 24 | 97.65 | 96.88 | 0.13 | 97.15 |
| Diluent II | | | | |
| 0 | 100.37 | 100 | — | 98.00 |
| 3 | 100.23 | 99.86 | 0.05 | 97.88 |
| 5 | 100.01 | 99.65 | 0.07 | 97.90 |
| 24 | 98.71 | 98.35 | 0.07 | 97.24 |
| Diluent III | | | | |
| 0 | 98.82 | 100 | — | 97.82 |
| 3 | 98.67 | 99.85 | 0.05 | 97.77 |
| 5 | 98.45 | 99.62 | 0.08 | 97.62 |
| 24 | 97.19 | 98.35 | 0.07 | 97.25 |
| Diluent IV | | | | |
| 0 | 101.94 | 100 | — | 98.37 |
| 3 | 101.68 | 99.75 | 0.08 | 98.30 |
| 5 | 101.50 | 99.57 | 0.09 | 98.30 |
| 45 | 100.46 | 98.55 | 0.06 | 97.93 |

TABLE 19

Potency and purity of a Salinosporamide A stored at 25° C. after reconstitution from a Salinosporamide A/sucrose lyophilate.

| Time (h) | Potency (%) | Recovery Based on time t = 0 | Degradation rate (%/h) | Purity (%) |
|---|---|---|---|---|
| Diluent I | | | | |
| 0 | 99.06 | 100 | — | 97.93 |
| 3 | 96.45 | 97.36 | 0.88 | 96.76 |
| 5 | 94.88 | 95.78 | 0.84 | 96.12 |
| 24 | 80.04 | 80.79 | 0.80 | 88.51 |
| Diluent II | | | | |
| 0 | 98.64 | 100 | — | 98.17 |
| 3 | 96.86 | 98.20 | 0.60 | 97.45 |
| 5 | 94.88 | 96.19 | 0.76 | 96.91 |
| 24 | 85.45 | 86.63 | 0.56 | 90.91 |
| Diluent III | | | | |
| 0 | 98.83 | 100 | — | 98.34 |
| 3 | 97.16 | 98.30 | 0.57 | 97.31 |
| 5 | 95.87 | 97.00 | 0.60 | 96.61 |
| 24 | 85.78 | 86.79 | 0.55 | 92.11 |
| Diluent IV | | | | |
| 0 | 98.81 | 100 | — | 98.44 |
| 3 | 97.32 | 98.50 | 0.50 | 97.72 |
| 5 | 96.26 | 97.42 | 0.52 | 97.14 |
| 24 | 86.15 | 87.19 | 0.53 | 92.44 |

Example 14

Stability Studies of Various Lyophilized Formulations and Dosing Solutions of Salinosporamide A To determine the stability of various lyophilized formulations of Salinosporamide A and the reconstituted dosing solutions, stability studies were carried out on various lots of lyophilized formulations prepared using sucrose, Kollidon 12 PF or 17 PF as excipient, and stored at −20, 5, 25, 40, and 50° C.

Drug Product Formulation Stability

Several lots of Salinosporamide A lyophile formulations were diluted with diluent containing various compositions of Propylene Glycol (PG), PEG 400, Citrate Buffer and EtOH. In a typical formulation preparation, Salinosporamide A lyophile was dissolved with an appropriate amount of diluent at 5 and 25° C. and mixed to obtain a clear solution of dose formulation. Stability studies of the formulations were conducted at 5 and 25° C. for comparison and formulation selection.

Results of accelerated stability of Salinosporamide A formulations prepared with Kollidon or Sucrose as excipients are shown in FIGS. 5 and 6. The stability of Salinosporamide A lyophile was monitored under accelerated conditions (40 and 50° C.). The % Purity of NPI-0052 decreases more rapidly with Kollidon as excipient. A main impurity peak, NPI-2083/0049 is formed with Kollidon excipient under accelerated conditions. Formulations prepared with Kollidon are less stable than formulations prepared with Sucrose. Therefore, a sucrose lyophile was selected for further development.

Figure 8:
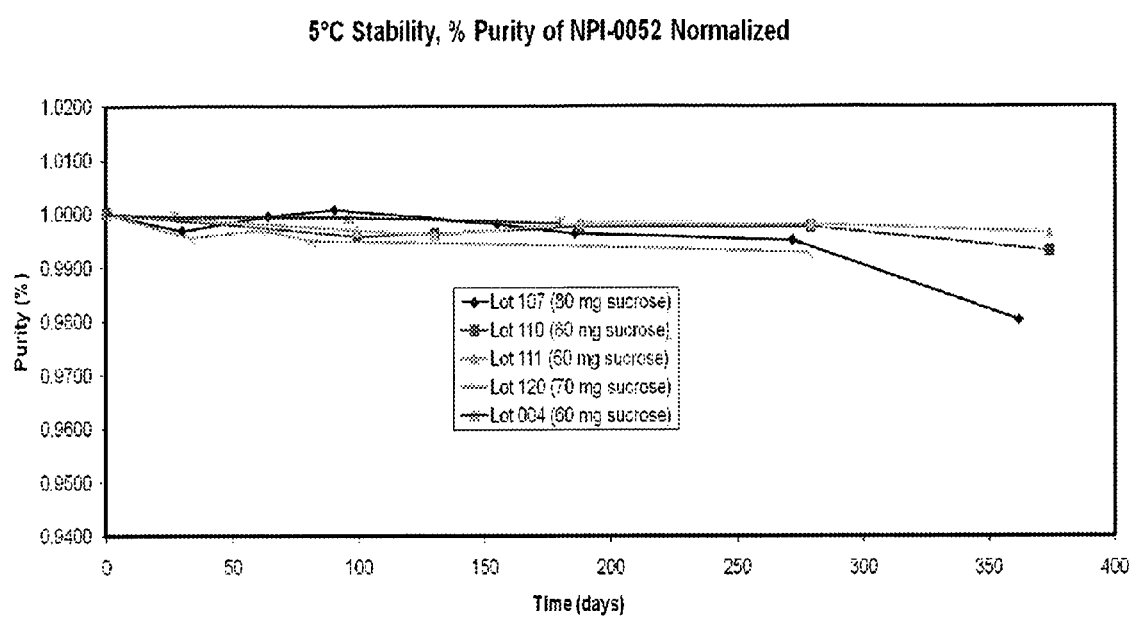
FIG. 8 is a graph showing long term stability results of various lyophilized Salinosporamide A formulations at 5° C., where Salinosporamide A purity was measured as a function of time.
Figure 9:
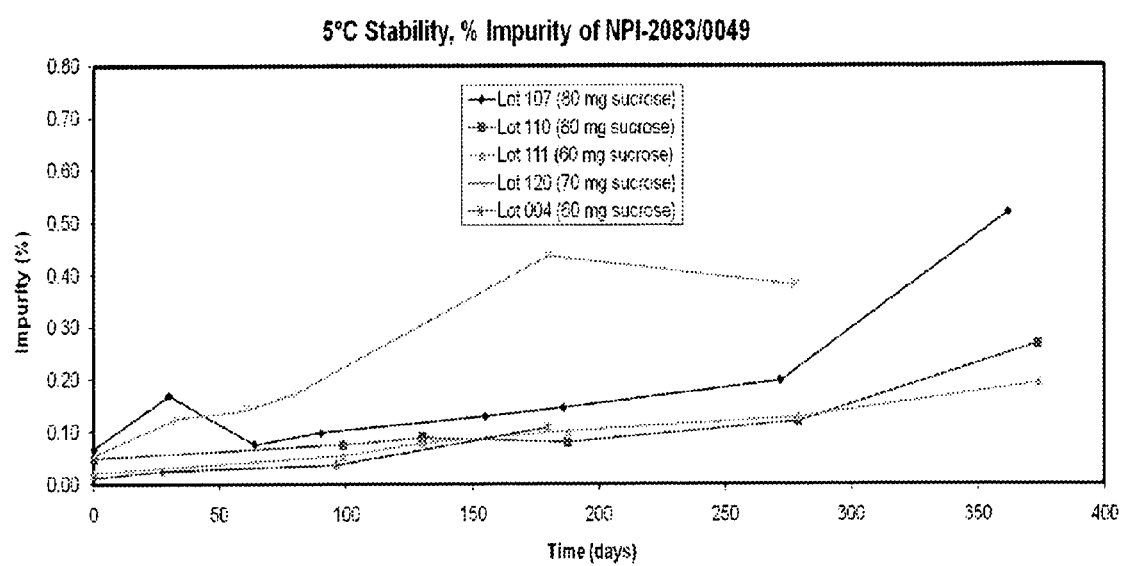
FIG. 9 is a graph showing long term stability results of various lyophilized Salinosporamide A formulations at 5° C., where the amount of the NPI-0049/2083 impurities was measured as a function of time.
Figure 10:
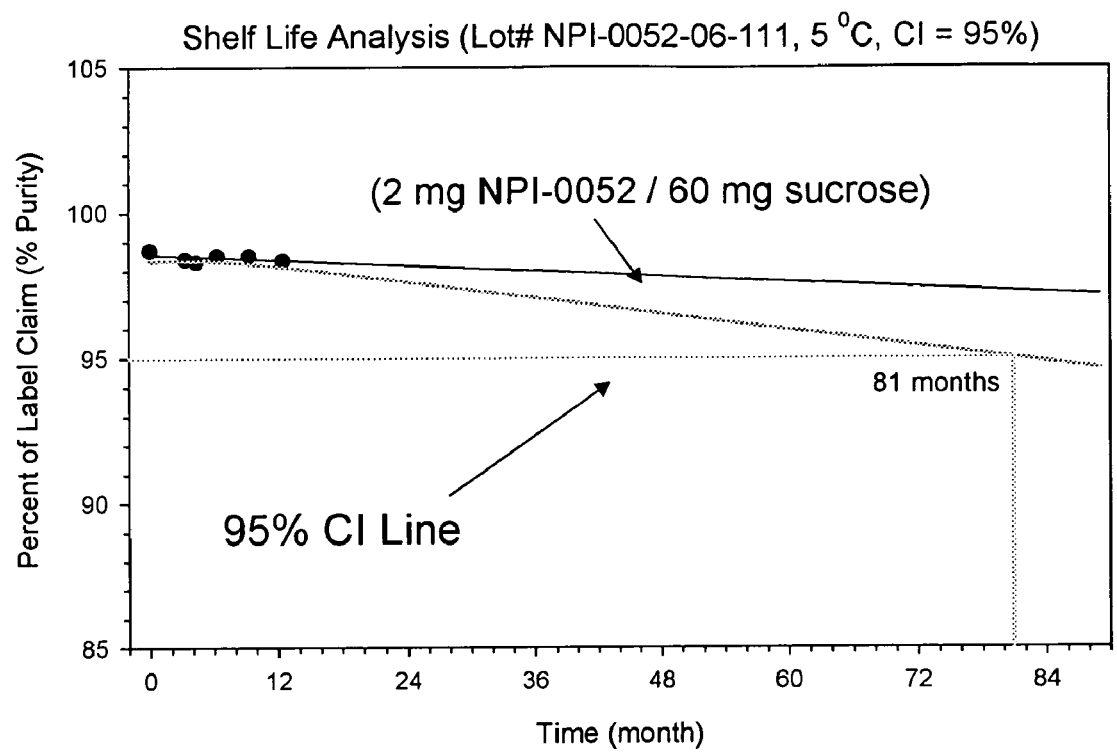
FIG. 10 is a graph showing a shelf life analysis of a lyophilized Salinosporamide A formulation (Lot # NPI-0052-06-111) stored at 5° C. with a confidence interval of 95%.

Long term stability results of Salinosporamide A lyophile drug product at 5° C. for up to 12 months are presented in FIGS. 8-10, and Tables 20-22. Vials were stored at −20, 5, 25° C. for stability analysis. Various lots of drug product with sucrose as excipient and varying compositions were prepared and stability studies were performed at −20, 5 and 25° C. For the formulations prepared with sucrose, the results suggest that within the range of sucrose tested, increasing the amount of sucrose lowers the stability. Based on the stability data, lyophile formulation with 2 mg/vial API and 60 mg/vial sucrose was selected as lead formulation. Stability data with shelf life prediction for the final formulation of Salinosporamide A (Lot # NPI-0052-06-111) stored at 5° C. with 95% confidence interval was evaluated. A shelf life of at least 81 months and 167 months at 5° C. and −20° C., respectively, is projected. Long term storage condition of 5° C. is proposed based on desired stability results for product shelf life.

TABLE 20

Compositions of Salinosporamide A for stability analysis.

| Salinosporamide A Drug Product Number | Salinosporamide A Composition (per vial) | |
|---|---|---|
| | NPI-0052 (mg) | Sucrose (mg) |
| NPI-0052-06-107 | 2.0 | 80 |
| NPI-0052-06-110 | 2.0 | 80 |
| NPI-0052-06-111 | 2.0 | 60 |
| NPI-0052-06-120 | 2.0 | 70 |
| NPI-0052-07-004 | 2.0 | 60 |

TABLE 21

Stability of Salinosporamide A Lot # NPI-0052-06-111

| | Purity (%) | | |
|---|---|---|---|
| Time (month) | 20 ± 2° C. | 5 ± 3° C. | 25 ± 2° C. |
| 0 | 98.69 | 98.69 | 98.69 |
| 1 | 98.57 | N/D | N/D |
| 3 | 98.43 | 98.39 | 97.87 |
| 4 | 98.57 | 98.3 | 97.71 |
| 6 | 98.63 | 98.52 | 97.87 |

TABLE 21-continued

Stability of Salinosporamide A Lot # NPI-0052-06-111

| | Purity (%) | | |
|---|---|---|---|
| Time (month) | 20 ± 2° C. | 5 ± 3° C. | 25 ± 2° C. |
| 9 | 98.69 | 98.51 | 97.67 |
| 12 | 98.56 | 98.34 | 97.53 |

N/D: Not determined

TABLE 22

Shelf life of Salinosporamide A Lot # NPI-0052-06-111

| Lyo DP Lot # NPI-0052-06-111 (2 mg NPI-0052/60 mg sucrose) | 20 ± 5° C. (month) | 5 ± 3° C. (month) | 25 ± 2° C. (month) |
|---|---|---|---|
| Projected Shelf Life | 167 | 81 | 28 |
| Recommended Shelf Life | 24 | 24 | 24 |

Dose Solution Stability Results

Figure 11:
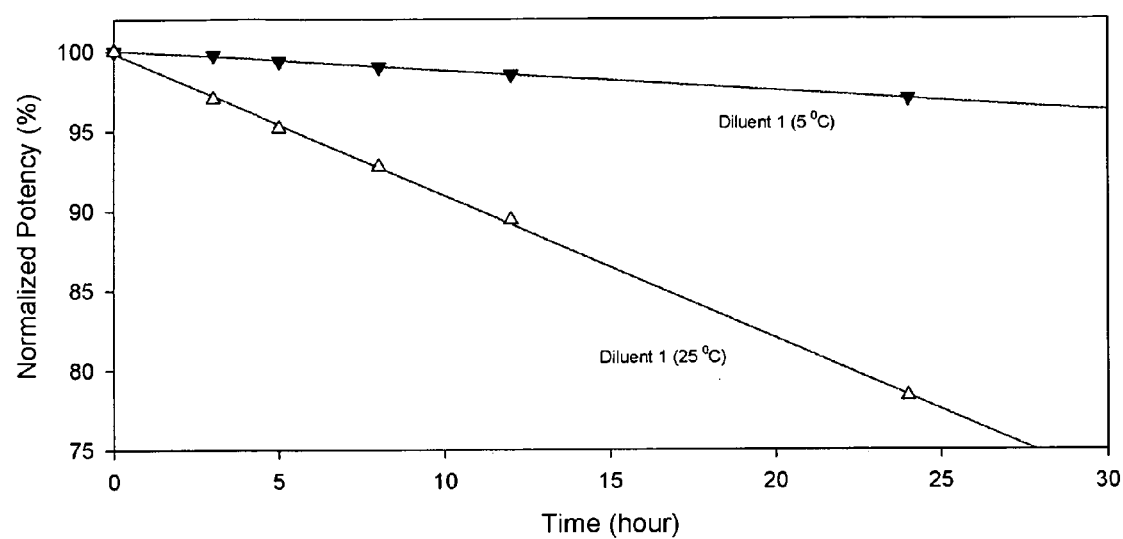
FIG. 11 is a graph showing results for % potency of dose solutions at 5° C. and 25° C. Diluent and dose solutions are indicated in Table 25.
Figure 12:
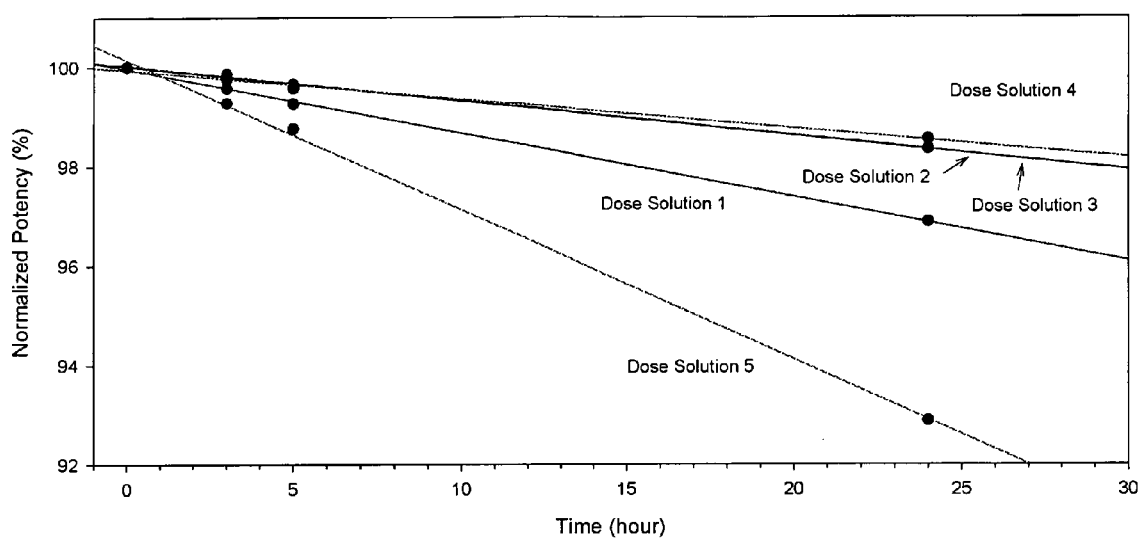
FIG. 12 is a graph showing results for % Potency of various dose solutions at 5° C. Dose solutions are indicated in Table 25.

Table 23 and FIGS. 11 and 12 describe the diluents evaluated for dose solution stability. NPI-0052 hydrolyzes in the presence of aqueous diluents. Stability studies were performed in various aqueous co-solvent systems at 5 and 25° C. to select dose solutions with sufficient stability to support practical use in the clinical setting. It is clear that the stability of dose solutions is best at 5° C. The final drug product diluent contains 40% PG/20% EtOH/40% CB. Although several diluents are more stable for up to 24 hours, the final drug product diluent was chosen based on stability, high total water content in the dose formulation as well as reconstitution time of less than 2 minutes.

Accelerated stability data indicated that formulation with sucrose as excipient is more stable than the formulation prepared using Kollidon as excipient. Further, stability studies suggested that a parenteral formulation of NPI-0052 lyophile reconstituted with 40% PG-40% CB-20% EtOH is stable for up to 24 hours at 5° C.

TABLE 23

Diluent selection for dose solution stability

| | Drug Product Diluent Composition (%, v/v) | | |
|---|---|---|---|
| NPI-0052 Drug Product Diluent | Ethanol | PG/PEG 400 | Citrate Buffer (10 mM, pH 5.0) |
| Diluent 1 | 20 | 40 (as PG) | 40 |
| Diluent 2 | 20 | 50 (as PG) | 30 |
| Diluent 3 | 20 | 40 (as PEG400) | 40 |
| Diluent 4 | 20 | 50 (as PEG400) | 30 |
| Diluent 5 | 10 | 40 (as PG) | 50 |

Example 15

Lyophilization Development of Salinosporamide A in a Water/T-Butyl Alcohol Co-Solvent Systems Process parameters affecting lyophilization and residual solvents, namely, water and t-butyl alcohol, were evaluated to develop a robust lyophilization process for water/tert-butanol co-solvent formulation containing sucrose and Salinosporamide A.

Salinosporamide A was formulated with 16-40 mg/mL sucrose in 12-16% water/tert-butanol (v/v) co-solvent systems. The formulation was filled in 20 mL flint tubing vials (Wheaton) and subsequently lyophilized to a dry powder for evaluation. A freeze dryer system (Virtis Genesis 25 SXL) with sample thief device was utilized for the studies. In-process samples were retrieved during the drying process and the sublimation rate of the lyophilization process was analyzed by percentage weight loss. The desorption rate and residual solvents content were determined by Karl Fischer Coulometric Titration (Mettler Toledo DL32) for moisture and GC headspace method (Hewlett-Packard 5970 MSD GCMS) for tert-butanol, respectively. Thermal characteristics of the drug solutions were analyzed by freeze-thaw cycle studies and sub-ambient Differential Scanning Calorimetry (DSC, TA Instruments Q1000). The morphology of the finished drug product was evaluated using DSC and X-ray powder diffraction (XRPD), Shimadzu XRD-6000.

Freeze-Thaw Studies

The water-tert-butanol co-solvent formulations containing sucrose as bulking excipient exhibit a freezing temperature at about −10° C. immediately after a super-cooling event at −18° C. to about −21° C. The freezing point of tert-butanol is depressed by water and sucrose to sub-zero temperature. This result supports the use of 5° C. loading temperature prior to lyophilization. The ice melting event from the thawing cycle is observed to start at about −7° C.

Sub-Ambient DSC

Figure 13:
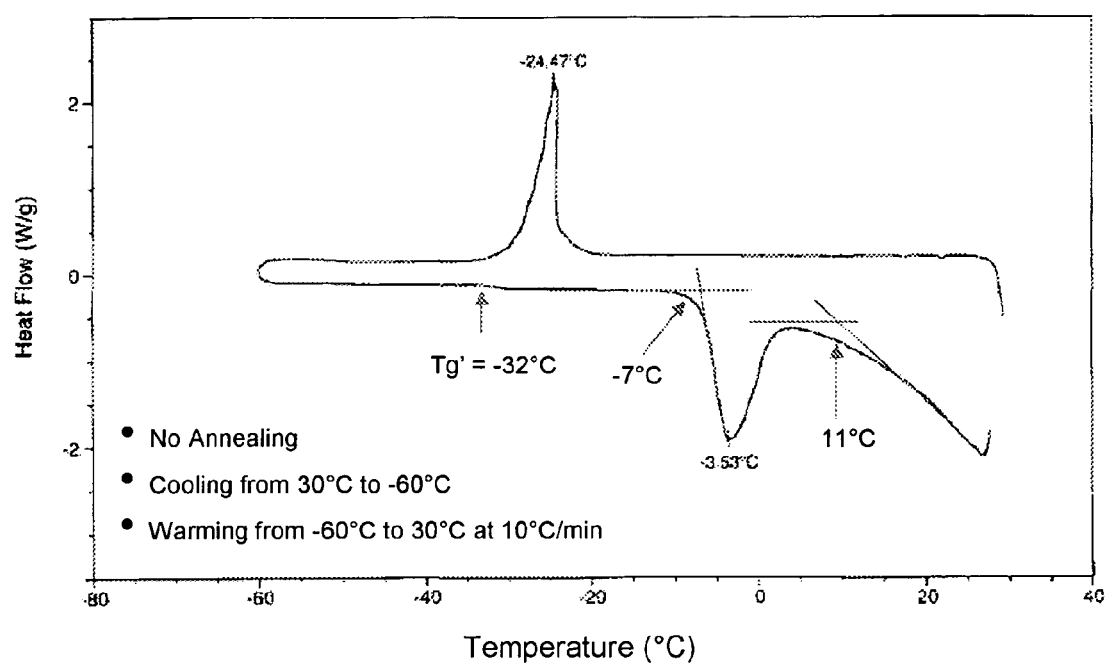
FIG. 13 is a graph showing a sub-ambient Differential Scanning Calorimetry thermograph for a Salinosporamide A formulation without an annealing step. The study was run at a rate of 10° C./min between 30° C. and −60° C. with an annealing temperature at −12° C. for 2 minutes.
Figure 14:
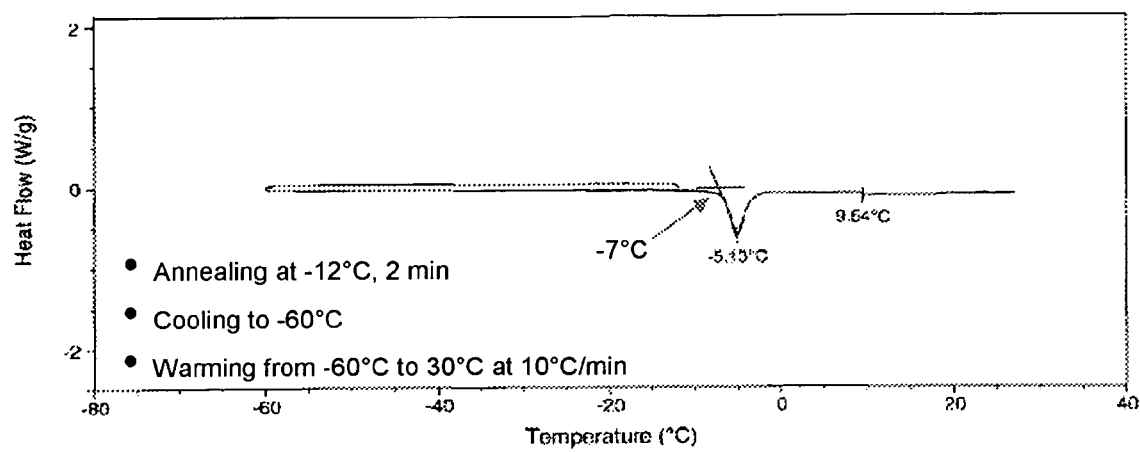
FIG. 14 is a graph showing a sub-ambient Differential Scanning Calorimetry thermograph for a Salinosporamide A formulation with annealing at −12° C. The study was run at a rate of 10° C./min between 30° C. and −60° C. with an annealing temperature at −12° C. for 2 minutes.

The studies were run at a rate of 10° C./min between 30° C. and −60° C. and with an annealing temperature at −12° C. for 2 minutes. The thermograph shows two on-set eutectic melting temperatures at −7° C. and 11° C., and an apparent glass transition temperature (Tg') of sucrose at about −32° C. After annealing step at −12° C., only one significant eutectic temperature at −7° C. is observed with no presence of Tg' (see thermographs in FIGS. 13 and 14).

Sublimation Rate

In-process samples were collected from the primary drying cycle when shelf temperature reached at −34° C. and −30° C. with vacuum pressure at 200 mtorr. The sublimation rate based on % weight loss was determined to be 0.10-0.12 g/hr or 0.04-0.05 $g/cm^2/hr$. It was observed that a high shelf temperature exceeding −24° C. can cause the cake matrix to vibrate and puff; this is because a high vapor pressure of tert-butanol and fast sublimation (mass transfer) can push the partially dry cake matrix upward before the primary drying cycle is complete. Therefore, the shelf temperature can advantageously be maintained at −31+/−3° C. during the primary drying cycle with constant chamber pressure, 200 mtorr, in this case, to avoid overheating of product temperature.

There is no appreciable change in weight loss for the secondary drying cycle especially after 30 hr. An extended $2^{nd}$ drying cycle at 25° C. or an elevated temperature does not significantly affect the % residual tert-butanol in the final drug product.

Figure 15:
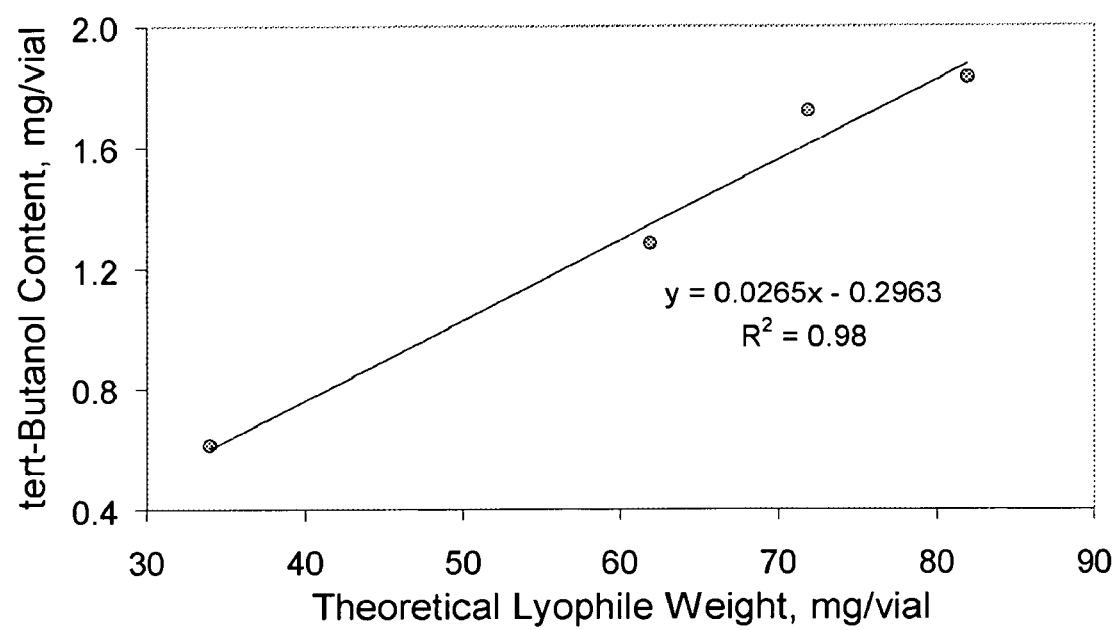
FIG. 15 is a graph showing a correlation between the residual tert-butanol of finished drug product per vial and the total lyophile weight per vial.

The lyophilization cycle for Salinosporamide A formulation started with pre-freezing at −45° C., an annealing step at −12° C., and $2^{nd}$ freezing step at −45° C. The shelf temperature was kept at −31° C. for 24 hr during primary drying and 25° C. for 30 hr during $2^{nd}$ drying, respectively, while chamber pressure was kept at 200 mtorr. The moisture content and residual tert-butanol of the finished drug products are tabulated in Table 24. Interestingly, the residual tert-butanol content was found to have a good linearly correlation to the theoretical total solid weight in the lyophile (see FIG. 15).

TABLE 24

% Residual Solvents of Salinosporamide A Lyophilized Products

| Solid Content in Lyophile Vial | $H_2O$ Content | | Tert-Butanol | |
|---|---|---|---|---|
| | (mg/vial) | (%, w/w) | (mg/vial) | (%, w/w) |
| 2 mg active with 32 mg Sucrose | n/a | n/a | 0.61 | 1.8 |
| 2 mg active with 60 mg Sucrose | 0.23 | 0.4 | 1.28 | 2.1 |
| 2 mg active with 70 mg Sucrose | 0.15 | 0.2 | 1.72 | 2.4 |
| 2 mg active with 80 mg Sucrose | 0.21 | 0.3 | 1.83 | 2.2 |

The DSC thermograph of the lyophile shows a Tg at 52° C., in good agreement with amorphous sucrose Tg at a low moisture environment. The lyophile was reconstituted with a co-solvent diluent within 2 minutes.

Example 16

Bulk Solution Solubility and Stability

A water-tert-butanol system with a suitable ratio was evaluated to accommodate both the drug and excipient solubility, as well as minimize the rate of hydrolysis for a lyophilization preparation.

Solubility and Stability Studies

Salinosporamide A solubility was determined in 100% tert-butanol (TBA) and in TBA containing 3% (w/v) Kollidon 12 PF and 3% (w/v) Kollidon 17 PF, respectively. Both Kollidons can dissolve in TBA at approximately 4% (w/v). 3% Kollidon can serve as the bulking agent to support a lyophilization preparation. Salinosporamide A was added and saturated in the vehicles at ambient room temperature overnight. Salinosporamide A solutions were filtered and analyzed by HPLC to determine the solubility.

Salinosporamide A in-situ phase solubility and stability were determined in 10, 20 and 30% $H_2O$-TBA (v/v) solutions. Salinosporamide A was prepared at 2 mg/mL in TBA as a stock solution. HPLC water was spiked into the Salinosporamide A solution aliquot to make up the equivalent 10, 20 and 30% $H_2O$-TBA solutions at room temperature. Each drug solution was mixed and immediately filtered. The filtrate was collected as time zero sample and analyzed by HPLC at real time to avoid drug degradation. The filtrate was subsequently sampled and filtered at 4, 24 and 48 hr to monitor drug stability at ambient room temperature.

Salinosporamide A solubility in 100% TBA was determined to be 2 mg/mL by HPLC. The drug is stable at ambient room temperature overnight. The drug solubility in 3% Kollidon 12 PF-TBA and 3% Kollidon 17 PF-TBA was determined to be 4.9 and 4.2 mg/mL, respectively. Both drug solutions were stable at room temperature overnight.

Figure 16:
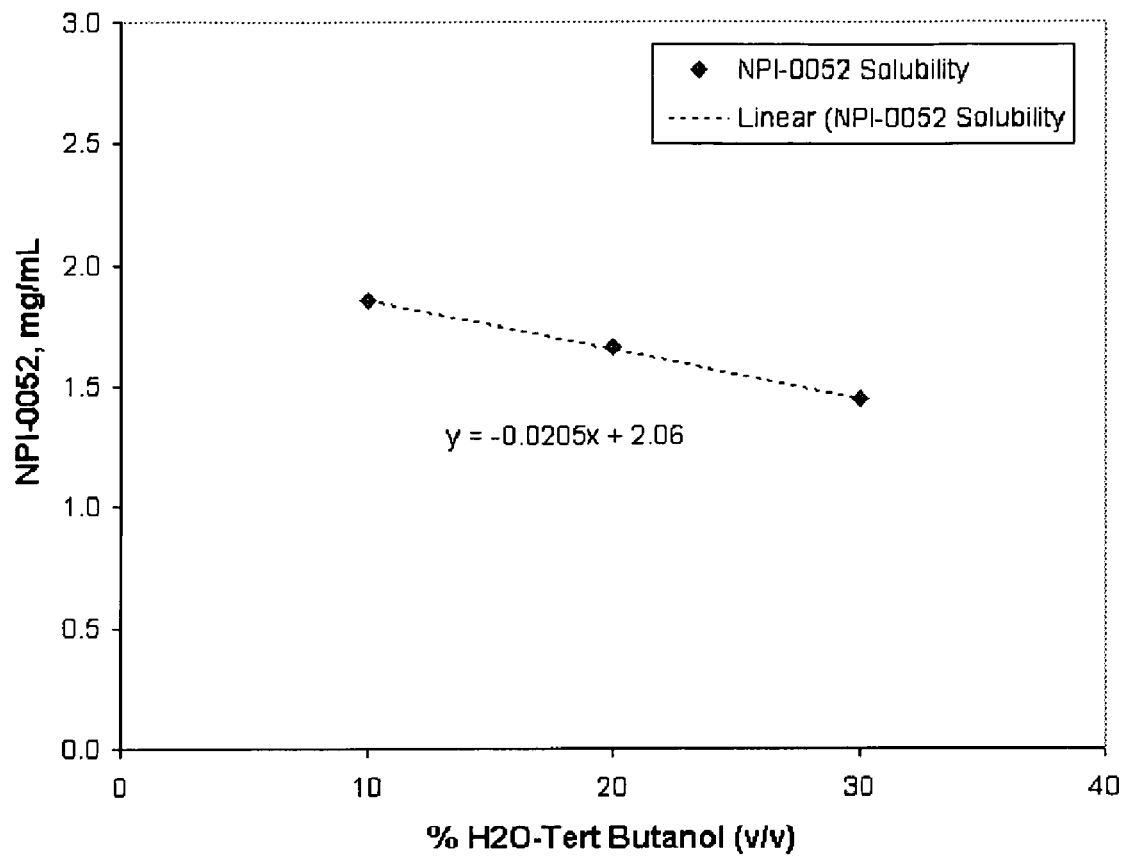
FIG. 16 is a graph showing Salinosporamide A in-situ phase solubility in 10, 20 and 30% $H_2O$-TBA (v/v) solutions. Salinosporamide A was prepared at 2 mg/mL in TBA as a stock solution. HPLC water was spiked into the Salinosporamide A solution aliquot to make up the equivalent 10, 20 and 30% $H_2O$-TBA solutions at room temperature.

Salinosporamide A in-situ phase solubility and stability in % $H_2O$-TBA are illustrated in FIG. 16 and Table 25. The results indicate that a stable bulk solution can be prepared at 1 mg/mL Salinosporamide A in the 10-30% $H_2O$-TBA co-solvent systems at room temperature.

TABLE 25

Salinosporamide A (NPI-0052) Stability in H₂O-TBA Co-solvent Systems

| Room Temp. Stability (hr) | HPLC Assay (% Purity) | | |
|---|---|---|---|
| | 10% H₂O-TBA | 20% H₂O-TBA | 30% H₂O-TBA |
| 0 | 100.0 | 100.0 | 100.0 |
| 4 | 99.5 | 99.8 | 99.8 |
| 24 | 99.8 | 99.8 | 99.5 |
| 48 | 99.7 | 99.7 | 99.3 |

Figure 17:
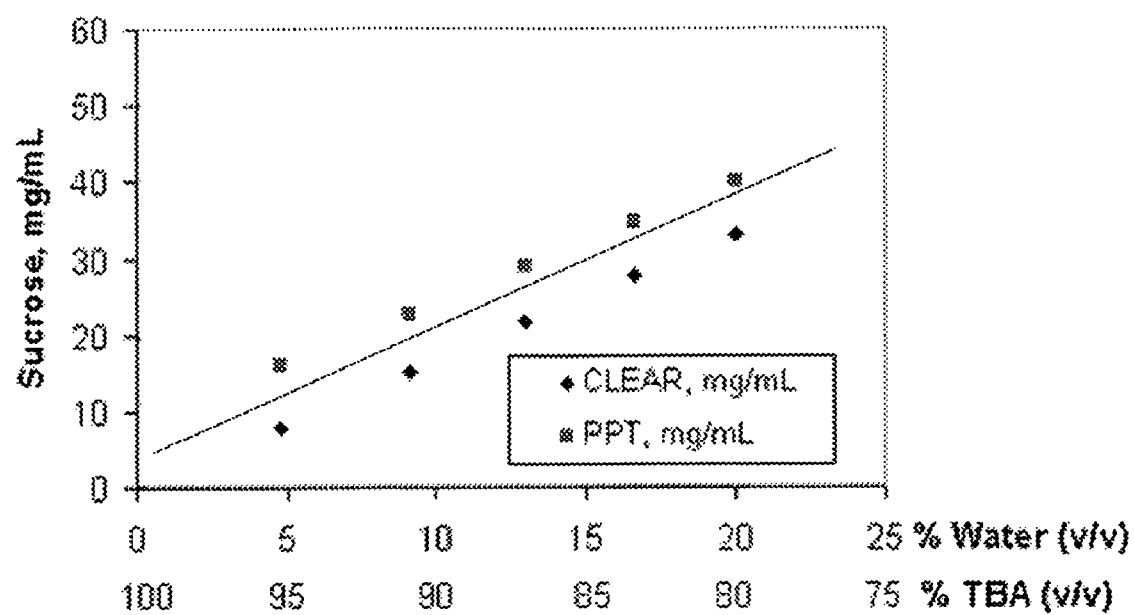
FIG. 17 is a graph showing sucrose in-situ phase solubility in % $H_2O$-TBA to determine the miscible zone and phase solubility for formulation development. The line represents the estimated sucrose solubility curve.
Figure 18:
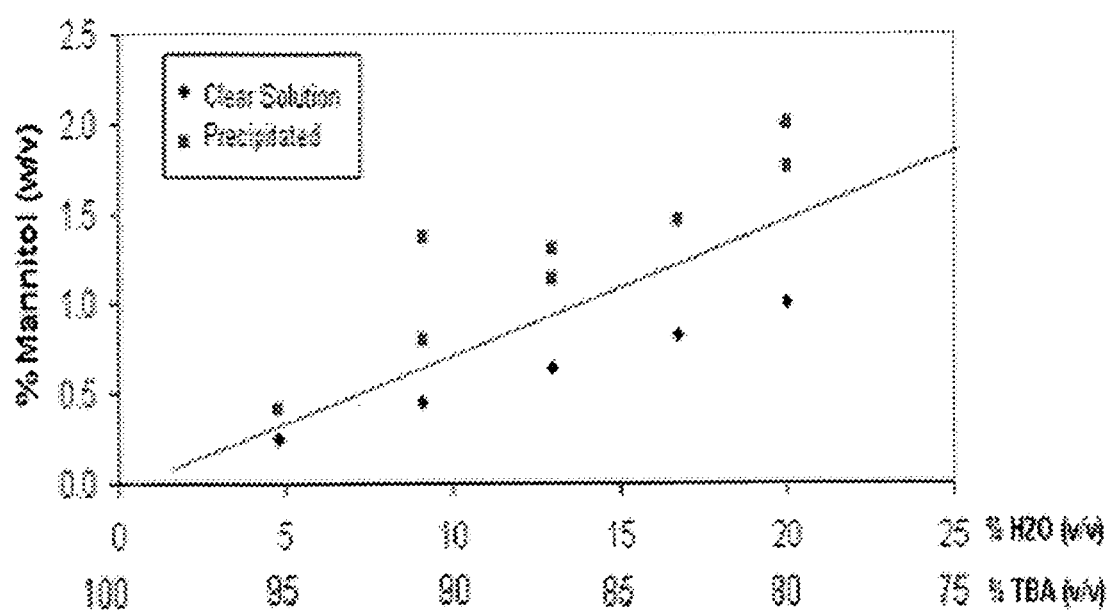
FIG. 18 is a graph showing mannitol in-situ phase Solubility in % $H_2O$-TBA to determine the miscible zone and phase solubility for formulation development. The line represents the estimated mannitol solubility curve.

Sucrose and mannitol in-situ phase solubility was conducted in various % H₂O-TBA co-solvent systems to determine the miscible zone for formulation development. Sucrose and mannitol in-situ phase solubility in % H₂O-TBA are illustrated in FIGS. 17 and 18, respectively. The miscible zones and the phase solubility curves are estimated. When sucrose is used as the bulking excipient, 3% sucrose will be soluble in TBA solution containing at least 14% H₂O in TBA; and 5% sucrose in at least 25% H₂O in TBA. When mannitol is used as the bulking excipient, 1% mannitol will be soluble in TBA solution containing at least 15% H₂O in TBA; and 1.8% mannitol in at least 25% H₂O in TBA, respectively. However, the lyophilized drug product containing mannitol does not yield acceptable reconstitution performance with diluent.

Sucrose Formulation Stability

Salinosporamide A was formulated with sucrose (as bulking excipient) in 14% H₂O-TBA as a clear solution prior to lyophilization. The bulk solution stability was monitored at 2-8° C. and 25° C. The solution was 2 mL filled in 20 mm 20 cc flint tubing vial and subsequently lyophilized to yield a white powder for stability evaluation.

Figure 19:
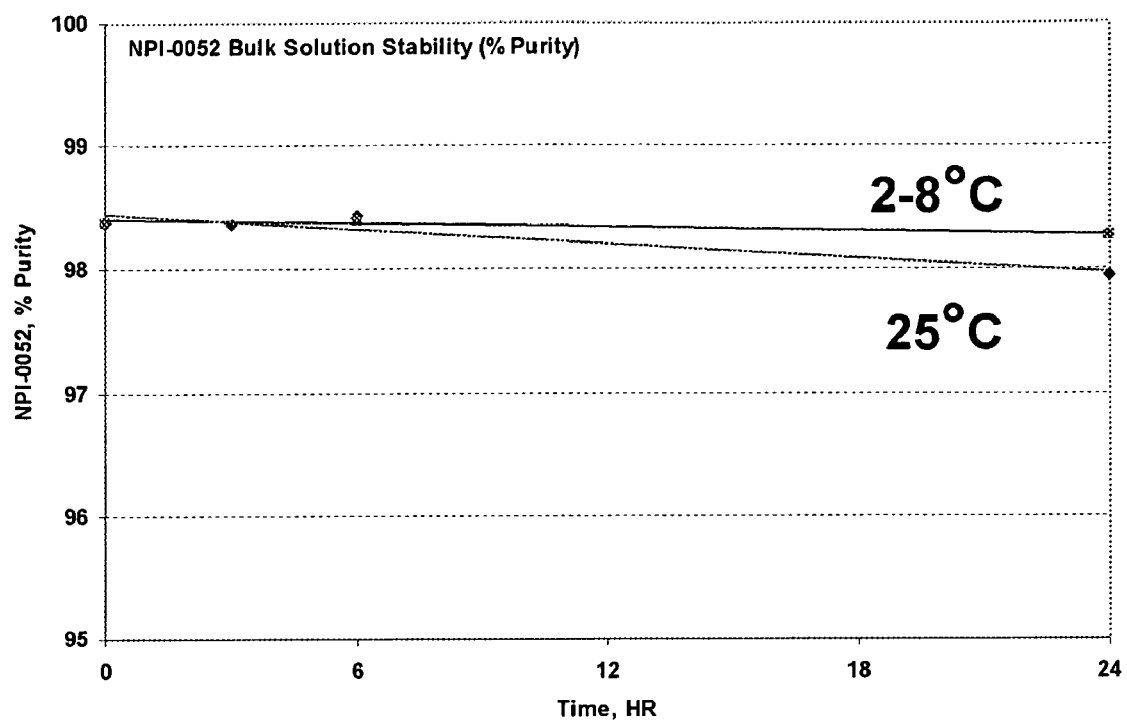
FIG. 19 is a graph showing Salinosporamide A bulk solution stability as a function of % purity over time at 2-8° C. and 25° C., for a bulk solution containing 1 mg/mL API with 35 mg/mL sucrose in 14% $H_2O$-TBA.
Figure 20:
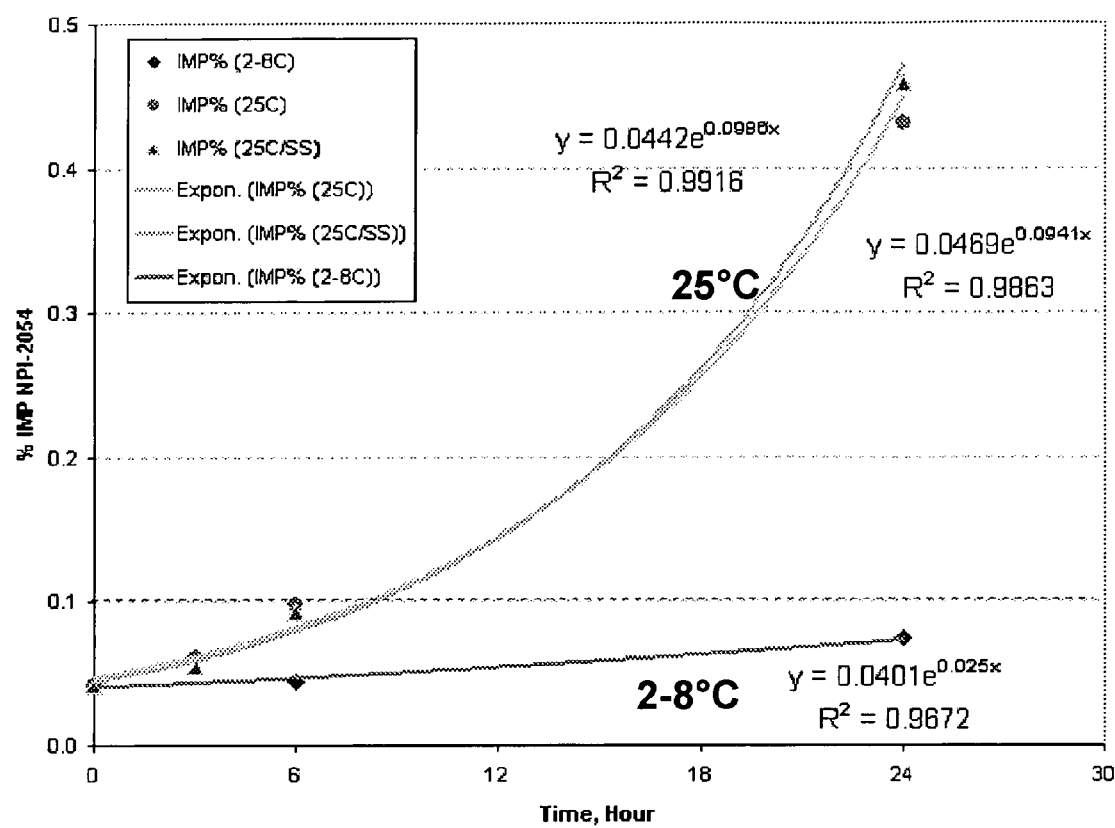
FIG. 20 is a graph showing Salinosporamide A bulk solution stability as a function of % degradant, NPI-2054, over time at 2-8° C. and 25° C., for a bulk solution containing 1 mg/mL API with 35 mg/mL sucrose in 14% $H_2O$-TBA.

As depicted in the graph of FIG. 19, Salinosporamide A bulk solution formulated with sucrose in 14% H₂O-TBA was stable at 2-8° C. for at least 24 hr and at 25° C. for at least 6 hr. respectively. As depicted in the graph of FIG. 20, the primary hydrolytic degradant (NPI-2054) can be controlled to less than 0.1% in the solution prior to lyophilization. This stability is sufficient to support product stability during the lyophile manufacturing process. The bulk solution was filled in the vial and lyophilized to yield a stable drug product with suitable reconstitution performance with diluent.

Thus, Salinosporamide A can be formulated with sucrose as bulking excipient in H₂O-TBA co-solvent system as a clear bulk solution prior to lyophilization. The lyophilization subsequently removes the solvents and produces a stable Salinosporamide A lyophile. The drug product has demonstrated satisfactory stability at 2-8° C. and can be readily reconstituted with a propylene glycol/Ethanol/Citrate buffer diluent to yield a ready-to-use solution for IV administration.

Although common bulking agents, such as sucrose or mannitol, have poor solubility in alcohols, the API solubility can be improved with an in-situ co-solvent approach prior to lyophilization.

The above example further demonstrates that any compound comprising a β lactone ring, such as Salinosporamide A, can be protected from hydrolysis during bulk solution compounding and lyophilization by using a lyophilization preparation from a TBA solvent or H₂O-TBA co-solvent system.

Although the invention has been described with reference to embodiments and examples, it should be understood that numerous and various modifications can be made without departing from the spirit of the invention. Accordingly, the invention is limited only by the following claims.

What is claimed is:

1. A lyophilized formulation comprising Salinosporamide A and a bulking agent comprising sucrose.

2. A container comprising a lyophilate comprising Salinosporamide A and a bulking agent comprising sucrose.

3. The container of claim 2 comprising from about 0.2 mg to about 4 mg of Salinosporamide A.

4. The container of claim 2, wherein the container is selected from the group consisting of a type 1 flint tubing vial, an amber tubing vial, a clear molded vial, and an amber molded vial.

5. A kit for administering Salinosporamide A comprising:
   a first container comprising a lyophilate comprising Salinosporamide A or an analog thereof and a bulking agent comprising sucrose; and
   a second container comprising a diluent.

6. The kit of claim 5, wherein the bulking agent comprises from about 10 mg to 100 mg of sucrose.

7. The kit of claim 5, wherein the first container comprises from about 0.2 mg to about 4 mg of Salinosporamide A.

8. The kit of claim 5, wherein the first container is selected from the group consisting of a type 1 flint tubing vial, an amber tubing vial, a clear molded vial, and an amber molded vial.

9. The kit of claim 5, wherein the diluent comprises a co-solvent system.

10. The kit of claim 5, wherein the diluent comprises polyethylene glycol, ethanol, a buffer, or mixtures thereof.

11. The kit of claim 10, wherein the buffer is a citrate buffer.

12. The kit of claim 5, wherein the diluent comprises propylene glycol, ethanol, a buffer, or mixtures thereof.

13. The kit of claim 12, wherein the buffer is a citrate buffer.

14. The kit of claim 5, wherein the diluent comprises at least 50% propylene glycol, ethanol, and 40% citrate buffer (10 mM, pH 5.0).

* * * * *

UNITED STATES PATENT AND TRADEMARK OFFICE
CERTIFICATE OF CORRECTION

PATENT NO. : 7,824,698 B2
APPLICATION NO. : 12/025679
DATED : November 2, 2010
INVENTOR(S) : Barbara Potts et al.

It is certified that error appears in the above-identified patent and that said Letters Patent is hereby corrected as shown below:

At Page 2, Column 1, Line 14, change "WO 2006/028525" to --WO 2005/028525--.

At Page 2, Column 2, Line 14, change "Actionmycetes" to --Actinomycetes--.

At Page 2, Column 2, Line 14, change "Leeuwenoek" to -- Leeuwenhoek--.

At Page 2, Column 2, Line 16, change "Activites" to --Activities--.

At Page 3, Column 1, Line 4, change "Discovey" to --Discovery--.

At Page 3, Column 1, Line 25, change "inhibiton" to --inhibition--.

At Page 3, Column 1, Line 54, change "Actinomycestes" to --Actinomycetes--.

At Page 3, Column 2, Line 15, change "FEMA" to --FEMS--.

At Page 3, Column 2, Line 36, change "Antinoflavoside" to --Actinoflavoside--.

At Page 3, Column 2, Line 61, change "or" to --of--.

At Page 4, Column 1, Line 40, change "Intracular" to --Intraocular--.

At Page 4, Column 1, Line 68, change "Antobiotico" to --Antibiotico--.

At Page 4, Column 2, Line 11, change "Olkawa" to --Oikawa--.

At Page 4, Column 2, Line 30, change "intergrated" to --integrated--.

At Page 4, Column 2, Line 53, change "Libopolysaccharide" to --Lipopolysaccharide--.

Signed and Sealed this
Fifth Day of July, 2011

David J. Kappos
*Director of the United States Patent and Trademark Office*

At Page 5, Column 1, Line 38, change "Mircrobiology" to --Microbiology--.

At Page 5, Column 1, Line 63, change "Hererologous" to --Heterologous--.

At Page 5, Column 2, Line 15, change "Actinomycestes" to --Actinomycetes--.

At Page 5, Column 2, Line 18, change "Cytotoix" to --Cytotoxic--.

At Page 5, Column 2, Line 26, change "Plaminogen" to --Plasminogen--.

At Column 3, Line 1, change "uretal," to --ureter,--.

At Column 5, Line 22, change "Salinospormide" to --Salinosporamide--.

At Column 9, Lines 55-63, change " " to -- --.

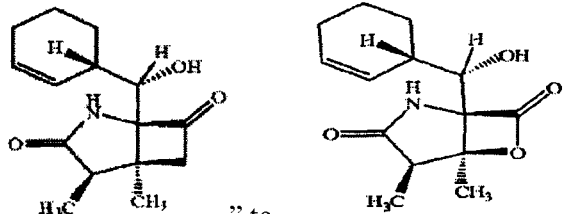

At Column 11, Line 60, change "tetrahydrofurn" to --tetrahydrofuran--.

At Column 12, Line 39, change "(2 injections" to --(2 injections)--.

At Column 12, Line 39, change "(2 injections" to --(2 injections)--.

At Column 12, Line 40, change "(2 injections" to --(2 injections)--.

At Column 12, Lines 40-41, change "(2 injections" to --(2 injections)--.

At Column 12, Line 41, change "(2 injections" to --(2 injections)--.

At Column 26, Lines 28-29, change "Salinosporamide A or an analog thereof and" to --Salinosporamide A and--.